United States Patent [19]

Harrison

[11] 4,353,626

[45] Oct. 12, 1982

[54] VISUAL RECOGNITION TESTING APPARATUS

[76] Inventor: Leslie H. R. Harrison, Orchard End, Furze Hill, Wimborne, Dorset, England

[21] Appl. No.: 115,765

[22] Filed: Jan. 28, 1980

[51] Int. Cl.³ .................................................. A61B 3/02
[52] U.S. Cl. .......................................... 351/36; 351/32
[58] Field of Search .............................. 351/32, 36, 37

[56] References Cited

U.S. PATENT DOCUMENTS 4,239,351  12/1980  Williams et al. ..................... 351/36

Primary Examiner—John K. Corbin
Assistant Examiner—Rodney B. Bovernick
Attorney, Agent, or Firm—Robert F. O'Connell

[57] ABSTRACT

Visual recognition testing apparatus is described which has a master array of individually selectable areas to be illuminated and a slave array of individual areas to be illuminated. A test sheet can be superimposed in front of the two arrays so as to show two sets of the same shapes differently arranged. The apparatus provides a controlled sequence of illumination of the shapes of a master array one after the other in response to correct choosing of corresponding shapes in the slave set of shapes by means of illumination of a chosen area of the slave array. A pupil controls illumination of the areas of the slave array and selection of a matching shape by settling on a chosen area of the slave array by the use of one or two switches. The apparatus processes the information conveyed by the use of these two switches in accordance with a given mode of operation and produces a decision indicating whether or not a correct choice has been made based upon comparison of the addresses of the illuminated areas of the master and slave arrays at choice by the pupil, comparison being effected by means of comparator means and teacher selected interconnections between two sets of terminals corresponding to the master and slave arrays. Success is communicated to the pupil by generation of a tune and failure by generation of a buzz. The addresses of the master and slave areas prevailing when a mistake is made are stored in a FIFO memory which is adapted to recall these mistakes at the arrays in response to a review signal after a test has been completed. The apparatus is particularly adapted for use with pupils suffering from damage or deficiency of the nervous system.

23 Claims, 20 Drawing Figures

VISUAL RECOGNITION TESTING APPARATUS

BACKGROUND TO THE INVENTION

This invention relates to apparatus for use in testing visual recognition, and especially for use in testing visual recognition in persons suffering from conditions which cause difficulty in their communicating with other people and possibly in their interpretation of their environment. For example, the apparatus may be particularly concerned with testing and thereby exercising the ability of a person suffering from cerebral palsy, or brain damage received in an accident after birth, or monogolism, to recognise shapes presented in a variety of ways, for example, with or without size constancy, in outline or as a dense figure, as a figure or as a background, when rotated or inverted, and so on, or to recognize words corresponding to representations of their referents, or numerals corresponding to countable assemblies of visual stimuli. The apparatus may also be used with pre-school children.

Although various teaching and testing apparatuses which provide visual stimuli for a pupil have been used for over a decade, such known apparatus has either been very limited in terms of adaption to a pupil or to the type of material presented, or very complex and requiring a teacher using the apparatus to have considerable skill in programming. An example of the more complex type of known apparatus is that described in an article entitled "A practical, low-cost, home/school microprocessor system" by Joe Weisbecker at pages 20 to 31 of the August 1974 issue of IEEE Computer and at pages 227 to 238 of "Microprocessors: Fundamentals and Applications", edited by Wen C Lin and published in 1976 by the IEEE Press of the Institute of Electrical and Electronics Engineers, Inc., of New York.

It is therefore an object of the present invention to provide an apparatus for use in testing visual recognition which apparatus is adapted to the abilities of disabled or immature pupils and can easily be used by an instructor to provide a variety of tests.

Another object of the invention is to provide an apparatus for use in testing visual recognition which apparatus allows an instructor to review errors made during a test after the test is completed.

SUMMARY OF THE INVENTION

The invention provides for the use of a mentally or physically disabled people or a young child an apparatus for use in testing and exercising the ability of such a pupil to effect the visual recognition, the apparatus having a first array of illuminating means which are individually selectable for energisation, and a second array of illuminating means which are also individually selectable for energisation. Master register means are coupled to the first array to select for energisation each illuminating means of the first array in accordance with a respective first predetermined sequence. Second register means are similarly coupled to the second array to select for energisation a chosen illuminating means of the second array. Mechanically controllable means are provided for causing the second register means to select for energisation in accordance with a respective second predetermined sequence a set of the illuminating means of the second array terminating with a chosen illuminating means and for establishing signals indicative of selection of the said chosen illuminating means. The apparatus further includes first and second arrays of terminals, the first array of terminals being representative of the first array of illuminating means and the second array of terminals being representative of at least some of the second array of illuminating means. Means are provided for interconnecting one or more pairs of these terminals, each of said one or more pairs of terminals comprising one terminal from each of the said arrays of terminals. Comparator means are coupled to the register means and to the interconnecting means and arranged thereby to compare the contents of the register means in a way which depends upon the manner of interconnection of the sets of terminals by the said interconnecting means. Logic circuitry is coupled to the comparator means and to the mechanically controllable means so that the comparator means is adapted to provide a first output signal in response to the said signal indicative of selection where there is correspondence between the contents of the second register means representing the chosen illuminating means and the contents of the first register means. The logic circuitry also provides a second output signal in response to the said signal indicative of selection when there is absence of such correspondence. A error memory is coupled to the register means and to the arrays of illuminating means and to the logic circuitry and is adapted to store the addresses of the selected illuminating means in the first array of illuminating means and the chosen illuminating means of the second array of illuminating means when the said second output signal is provided by the logic circuitry. Review means are furthermore provided which are coupled to the error memory and are actuable to cause the error memory to establish energisation of respective illuminating means in the said arrays thereof in accordance with the respective stored addresses. Thus mistakes, ie choices where there is absence of said correspondence, can be reviewed by an instructor after the apparatus has been used by the pupil. The invention furthermore provides an audio signal generating means coupled to the said logic means to generate a first audio signal in response to said first output signal and a second audio signal in response to said second output signal. Preferably the audio signal generating means comprises tune generating circuitry adapted to operate in response to said first output signal, and buzz generating circuitry adapted to operating response to said second output signal, whereby the first audio signal is a tune signal and the second audio signal is a buzz signal. The tune and buzz signals may be transduced by electroacoustic means to provide audible tunes and buzzes signifying respectively successes and failures.

In a preferred embodiment of the present invention the said logic circuitry includes means for supplying an advance signal and coupled to the first register means to effect an advance in the first predetermined sequence at the occurrence of each advance signal and being coupled to the second register means to effect resetting of the second register means to a start condition at each occurrence of each advance signal. The logic circuitry may also include means for supplying a reset signal to the second register means to effect resetting of the second register means to a start condition in response to each occurrence of the said second output signal.

In the preferred embodiment the said mechanically controllable means includes clock pulse generating means, gating means coupling said clock pulse generating means to said second register means and mechanically operable switch means connected to control said gating means so as to determine said second predetermined sequences. Said switch means may comprise mode switching means settable in any chosen one of a plurality of states, each such state determining a respective different form of said second predetermined sequence. The mechanically operable switch means also preferably includes at least one switch which, for at least one state of said mode switching means, is adapted to be operable to establish said signal indicative of selection.

Other objects, features and advantages of the present invention will be more readily understood from the detailed description of a preferred embodiment of the present invention which follows hereinafter with reference to the accompanying drawings.

DETAILED DESCRIPTION OF THE PREFERRED EMBODIMENT

Figure 1:
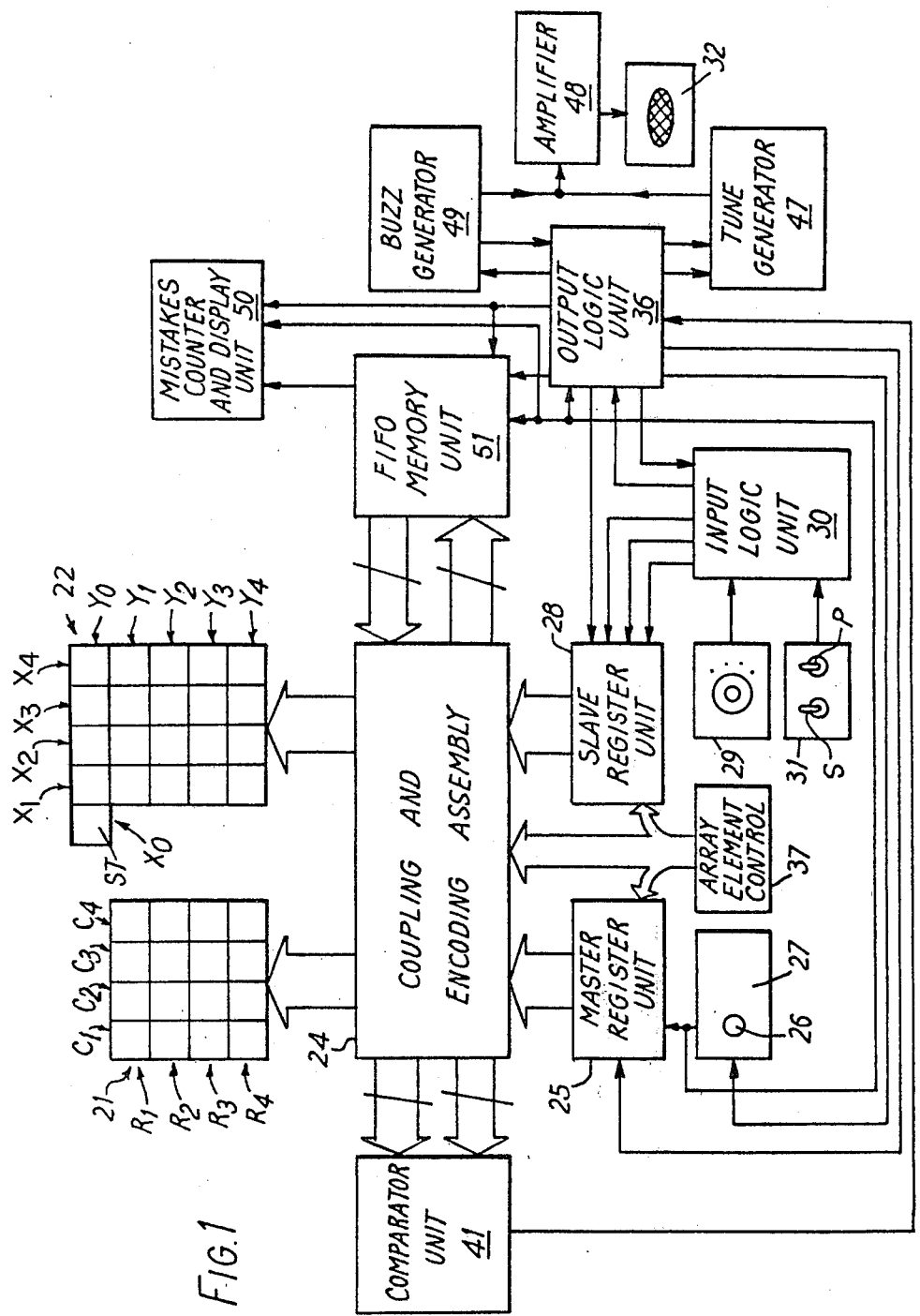
FIG. 1 is a block diagram of an apparatus for use in testing visual recognition in accordance with the present invention.

FIG. 1 of the accompanying drawings shows, in block form, an apparatus for use in testing visual recognition and embodying in preferred form the present invention. The preferred apparatus includes a first or master array 21 of sixteen areas arranged in a square with four columns $C_1$, $C_2$, $C_3$, and $C_4$ and four rows $R_1$, $R_2$, $R_3$, and $R_4$. Each of these sixteen areas can be individually illuminated. The apparatus also includes a second or slave array 22 of twenty one areas arranged, as shown, as a square of sixteen with a row of five areas above. The sixteen areas of the slave array arranged in a square are identified by respective column coordinates $X_1$, $X_2$, $X_3$ and $X_4$ and row coordinates $Y_1$, $Y_2$, $Y_3$ and $Y_4$. The additional row of five areas has a row coordinate $Y_0$ and the first area of this row is identified as a start area ST with coordinates $X_0Y_0$. Each of the twenty one areas of the slave array can be individually illuminated.

Figure 2:
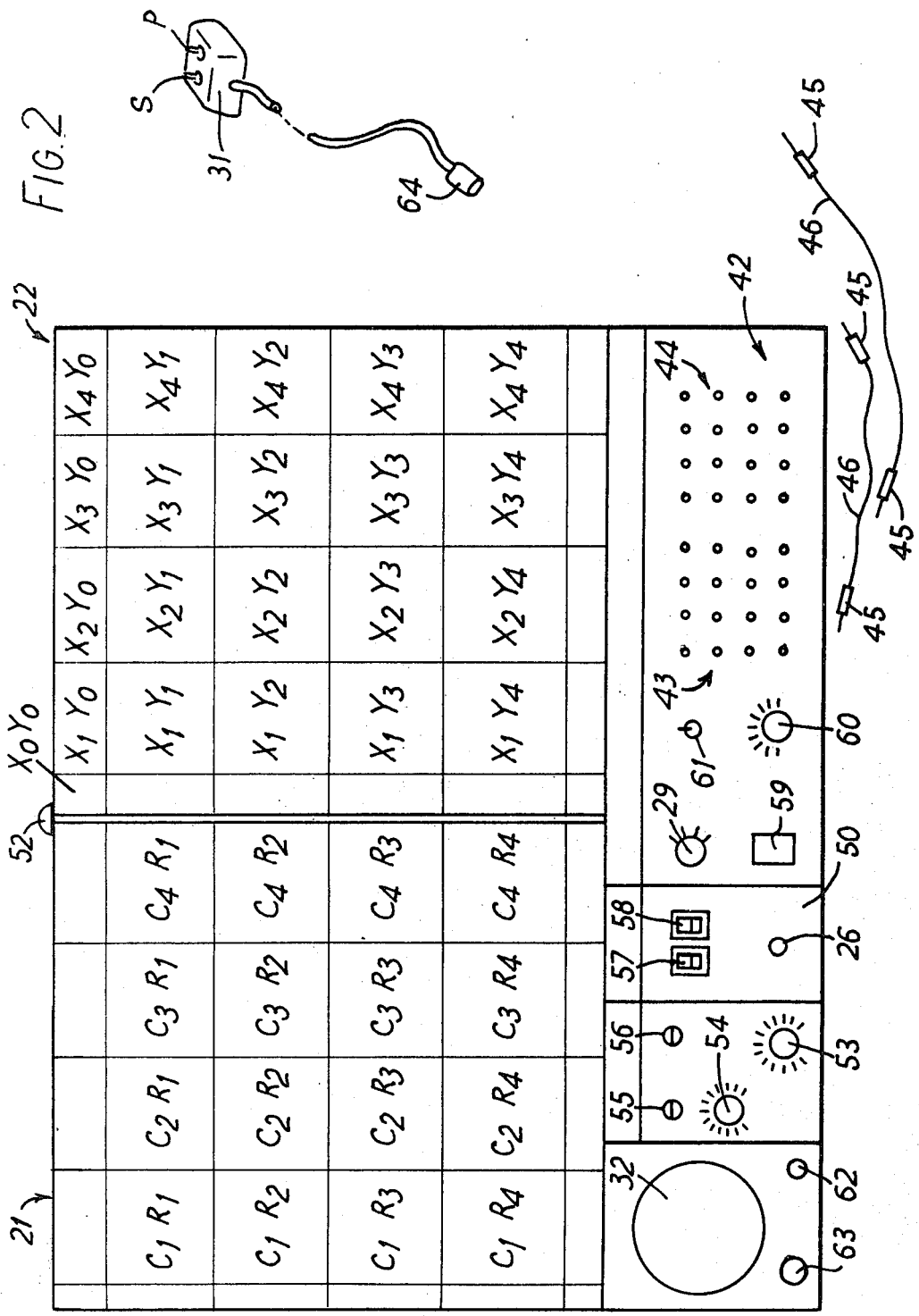
FIG. 2 is a front view of the housing of the apparatus of FIG. 1 together with elements to be connected thereto.

FIG. 2 shows the front of the main housing 23 of the apparatus of FIG. 1. A suitably marked out sheet of translucent plastics material defines the sixteen areas of the master array 21, and a similar marked out sheet defines the twenty one areas of the slave array 22. For reference only the respective coordinates of these areas are indicated in FIG. 2.

Referring again to FIG. 1, it will be seen that a master register unit 25 is coupled through a coupling and encoding assembly 24 to the master array 21. When operating, the master register unit initially causes the area $C_1R_1$ to be illuminated and thereafter, as will be explained hereinafter, causes the remaining fifteen areas of the master array 21 to be illuminated one after the other so that a predetermined sequence, namely, a sequential scan sequence, is followed in which each area of the first row $R_1$ is illuminated in the order $C_1R_1$, $C_2R_1$, $C_3R_1$, $C_4R_1$, then each area of the second row $R_2$ in the order $C_1R_2$, $C_2$, $R_2$, $C_3R_2$, $C_4R_2$ and so on until the area $C_4R_4$ is reached. To achieve such operation, the master register unit 25 comprises two shift registers which serves as a column register and a row register respectively and each of these registers circulates the binary condition 1000, as will be described hereinafter in more detail. The master array 21 can be reset to the state in which the area $C_1R_1$ is illuminated by manually closing a push button review switch 26 of a review unit 27 which is connected to the master register unit 25 to supply a master reset signal thereto in response to closure of the review switch 26.

A slave register unit 28 is similarly coupled to the slave array 22 through the coupling and encoding assembly 24. The slave register unit 28 can be operated in any chosen one of four different modes in accordance with whichever one of four different settings of a manually operable rotary mode switch 29 is chosen, the mode switch 29 being coupled to an input logic unit 30 which supplies clock pulses, and a mode signal to the slave register unit 28. At the start of any of the four modes of operation, the slave register unit 28 causes the start area ST of the slave array 22 to be illuminated, but what happens next depends on the mode chosen. The four modes differ from one another to provide four different grades of difficulty in control of the illumination of the individual areas of the slave array 22 by a pupil. The most difficult mode is referred to hereinafter as mode 1 and the simplest as mode 4, the other two, modes 2 and 3 being of intermediate difficulty. The modes also fall into two classes, one class comprising the modes 1 and 2 and the other class the modes 3 and 4.

In mode 3, as soon as the mode is chosen the individual areas of the array 22 start an initial sequential scan beginning at the area ST and progressing along the row $Y_0$ from ST to $X_4Y_0$, and then along the row $Y_1$ from $X_1Y_1$ to $X_4Y_4$ and so on until $X_4Y_4$ is reached, if the pupil does not stop the scan on an earlier area. If the mode 4 is allowed to continue in operation after $X_4Y_4$ has been reached, the next area to be illuminated is $X_1Y_1$ and the scan continues through $X_2Y_1$ and so on, row by row, until $X_4Y_4$ is again reached, if allowed. The scan again returns to $X_1Y_1$ to repeat the scan of the sixteen areas $X_1Y_1$ to $X_4Y_4$ until a choice of stopping point is acted on by the pupil. Thus after the initiation of mode 3 operation, no areas of the top row $Y_0$ are illuminated again. To enable a pupil to communicate a choice of stopping point to the slave register unit 28, a selector switch unit 31 is provided which is coupled to the input logic unit 30. The selector switch unit 31 has two mechanically operable on-off switches S and P, which in this preferred example are shown as manually operable, each having a conventional switch lever. Other forms of the switches S and P may be provided to suit the ability of a pupil to control the switches. For example, the mechanically operable switches S and P may be pneumatically actuatable, the switch S being closed when a pupil is sucking at a suitable mouthpiece and the switch P being closed when the pupil is puffing into the mouthpiece.

To communicate a choice of stopping point in mode 3, the switch S is closed. The choice thus made is then immediately tested in this mode and the pupil informed of success or failure by the production of a tune for success or a modulated buzz giving a "raspberry" effect for failure at a loudspeaker 32. Mode 4 has the same scanning sequence but provides easier control for the pupil in that the scan does not start until the switch S is closed and only continues while the switch S is closed, and no choice is communicated until the switch P is closed. Thus in mode 4, by operating the switch S the pupil can ensure that the chosen area of the slave array 22 is illuminated at the time that the choice is communicated by means of the switch P. It will be noted that in mode 4, before the switch P is closed, the scan can be stopped at any area of the sixteen $X_1Y_1$ to $X_4Y_4$ and will continue from the area on which it stopped if the switch S is again closed before the switch P is closed. Closure of the switch P results in testing of the choice and scanning can only begin again from the reset to the start area ST which occurs immediately the result of the test has been communicated by a tune or a buzz to the pupil. For some pupils, mode 4 is easier to use than mode 3 in which a choice must be communicated during the time that the chosen area is illuminated during the automatic scanning.

In mode 2, the start area ST remains illuminated until the switch S is closed whereupon the areas $X_1Y_0$, $X_2Y_0$, $X_3Y_0$ and $X_4Y_0$ are illuminated one after the other if the switch S remains closed for sufficient time. If the switch S is again closed or remains closed for longer than the clocked duration for the area $X_4Y_0$, the area $X_1Y_0$ is illuminated and the sequences $X_1Y_0$ to $X_4Y_0$ is followed until the switch S is opened. One of the areas $X_1Y_0$ to $X_4Y_0$ will therefore be held in the illuminated state when the switch S is opened. Subsequent closure of the switch P results in scanning of the four areas of the column having the previously held illuminated areas at its head. For example, if the area illuminated when the switch S opened is $X_3Y_0$, closure of the switch P then results in illumination of the areas $X_3Y_0$, $X_3Y_1$, $X_3Y_2$, $X_3Y_3$, $X_3Y_4$ in that order if the switch P is closed for sufficient time. If the switch P is again closed or remains closed for a sufficient time, the area $X_3Y_1$ is illuminated after the area $X_3Y_4$ and then the areas $X_3Y_2$, $X_3Y_3$ and $X_3Y_4$ are illuminated one after the other until the switch P is opened. Thus by first closing and opening the switch S to select a column, and then closing and opening the switch P to select one area of the selected column, a particular area among the sixteen areas $X_1Y_1$ to $X_4Y_4$ can be chosen. Errors in the choice of column can be corrected provided they are dealt with before the switch P is closed. Subsequent errors in the choice of area within the column can also be corrected provided they are dealt with before the choice is communicated by the pupil by closing the switch S after the final opening of the switch P.

In mode 1 the initial part of the scanning sequence is as in mode 2, ie by closing the switch S to select a column. However, there is no opportunity to correct a mistake in the choice of column since in mode 1 the opening of the switch S automatically results in the other part of the scan, ie the four areas of the chosen column are repeatedly illuminated in descending order. Furthermore, there is no opportunity to correct a mistake in the choice of one area of the chosen column since to stop the scanning of the column, the switch S must be closed again and this automatically communicates the choice in this mode and results in the pupil being informed of success or failure by the tune or the "raspberry" respectively.

Figure 3:
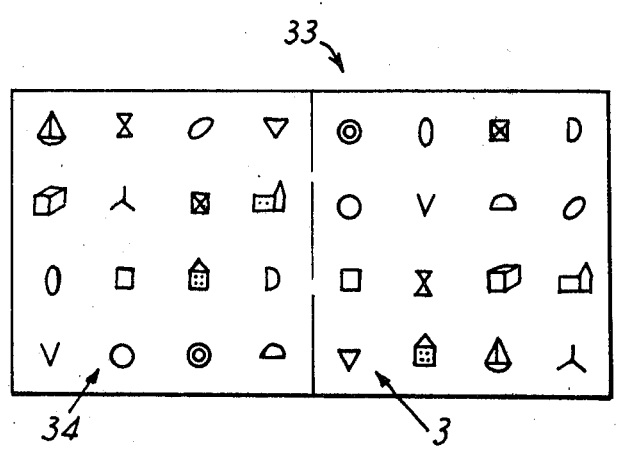
FIG. 3 is a representation of a test sheet for use with the apparatus of FIGS. 1 and 2.

FIG. 3 illustrates a visual recognition test sheet 33 for use with the apparatus of FIGS. 1 and 2. The test sheet 33 fits into the front of the main housing 23 of the apparatus so as to position a square master set 34 of sixteen shapes in register with the sixteen areas $C_1R_1$ to $C_4R_4$ and a square slave set 35 of the same sixteen shape in register with the sixteen areas $X_1Y_1$ to $X_4Y_4$. The positions of corresponding shapes in the sets 34 and 34 are different so that as each shape of the master set 34 is illuminated, the test sheet 33 being transparent or translucent, a pupil must search the slave set 35 visually to find the corresponding shape. For example, the shape at $C_1R_1$ is at $X_4Y_3$. The apparatus of FIG. 1 includes an output logic unit 36 which supplies a clock pulse to the master register unit 25 whenever a pupil makes a correct choice of area in the slave array 22 so that the next shape in the predetermined sequence applied to the master set 34 is illuminated and the pupil is able to indicate a choice in the slave set 35 to correspond to this next master shape. For example, if the pupil correctly indicates $X_4Y_3$ as the choice for the master shape at $C_1R_1$ the master shape at $C_2R_1$ is illuminated and the pupil must choose again. The correct response would then be $X_2Y_3$ for the test sheet 33 and would result in illumination of the master shape at $C_3R_1$. If the pupil indicates an incorrect choice, the master register unit 25 remains in the same state so that there is no change of the master shape illuminated, but the slave register unit 28 is reset by the output logic unit 36 so that the pupil can have another attempt. Further attempts are allowed for further wrong choices and this continues until the correct choice is made whereupon the next master shape is illuminated.

Figure 4:
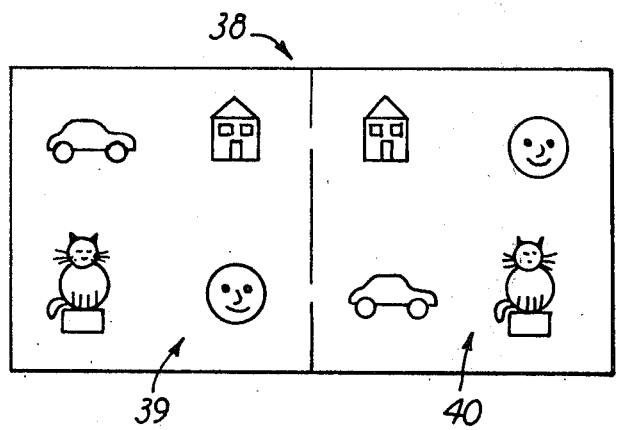
FIG. 4 is a representation of another test sheet for use with the apparatus of FIGS. 1 and 2.

The apparatus includes an array element control 37 coupled to the register units 25 and 28 and through the assembly 24 to the arrays 21 and 22. This control 37 has two states. In one state of the control 37, the arrays 21 and 22 are operated with sixteen and twenty-one individual areas as described hereinbefore. In its other state, the control 37 combines elements of the arrays 21 and 22 in pairs and modifies the operation of the register units 25 and 28 in such a way that the master array 21 operates as a four element array, each element corresponding to four of the sixteen original areas, and the slave array 22 operates as a seven element array, the seven elements being ST, $X_1Y_0$ with $X_2Y_0$, $X_3Y_0$ with $X_4Y_0$, and the sixteen areas $X_1Y_1$ to $X_4Y_4$ operating as four groups of four, namely, $X_1X_2Y_1Y_2$, $X_3X_4Y_1Y_2$, $X_1X_2Y_3Y_4$ and $X_3X_4Y_3Y_4$. FIG. 4 shows a test sheet 38 having a master set 39 of four shapes and a slave set 40 of the same four shapes scrambled relative to the master set 39.

Referring again to FIG. 1 it will be seen that coupled to the assembly 24 there is a comparator unit 41. The assembly 24 supplies the comparator unit 41 with two sets of signals respectively representing the respective contents of the master and slave register units 25 and 28. The comparator unit 41 compares these two sets of signals with one another in such a way that a comparison output signal supplied by the comparator unit 41 to the output logic unit 36 is indicative of whether or not the respective areas of the master and slave arrays 21 and 22 illuminated at the time of comparison constitute a correct choice of areas as defined by the test sheet, such as the sheet 33 of FIG. 3, being used. To enable the comparator unit 41 to carry out such an operation, it includes a patchboard 42, shown in FIG. 2 at the front of the main housing 23, consisting of two sets of sixteen socket-terminals 43 and 44 corresponding respectively to the areas $C_1R_1$ to $C_4R_4$ and $X_1Y_1$ to $X_4Y_4$, and sixteen pairs of jack plugs 45, each pair being electrically connected together by an insulated wire conductor 46, two such pairs being illustrated in FIG. 2, so that each socket-terminal of the set 43 can be connected to a selected socket-terminal of the set 44. An instructor can interconnect the set 43 with the set 44 in a way which corresponds to the pairs of positions of the matching master and slave shapes of a test sheet such as the sheet 33. Groups of four of the terminal-sockets are similarly interconnected to represent a test sheet such as the sheet 38. The comparator unit 41 includes circuitry which converts the set of signals representing the contents of the master register unit 25 into sixteen binary signals applied respectively to the terminal set 43 and which converts the set of signals representing the contents of the slave register unit 28 into sixteen binary signals applied respectively to the terminal set 44. Whenever two sets of binary signals as applied through the sixteen conductors 46 are identical, the comparator unit 41 indicates to the output logic unit 36 that a correct choice is present. If the two sets of binary signals as thus applied are not identical, the comparator unit 41 indicates to the output logic unit 36 that a wrong choice is present. The signal supplied by the unit 41 to the unit 36 is only required when a choice is actually made and therefore the unit 36 responds to the signal from the unit 41 only in the presence of a signal from the input logic 30 indicating that a choice is made.

If the signal supplied by the comparator unit 41 to the output logic unit 36 indicates a correct choice, the output logic circuit 36 supplies a pair of enabling signals to a tune generator 47 which for the duration of these enabling signals generates an audio frequency analogue of a tune and supplies this tune analogue to an amplifier 48 coupling the audio output of the tune generator 47 to the loudspeaker 32. The output logic unit 36 includes a timing circuit which determines the duration of the said pair of enabling signals. When the tune enabling signals, and hence the tune, terminate, the output logic unit 36 supplies a resetting signal to the slave register unit 28 and a sequence stepping signal to the master register unit 25, to reset the slave array 22 to area ST and to advance the master array 21 to the next area, and a choice reset signal to the input logic unit 30 to reset the input logic unit to the condition for making a fresh choice. However, if the signal supplied by the comparator unit 41 to the output logic unit 36 indicates a wrong choice, the output logic unit 36 applies a triggering signal to a buzz generator 49 which thereupon generates a modulated buzz analogue signal which it supplies to the amplifier 48 so that the loudspeaker 32 produces the "raspberry". The buzz generator includes a buzz timing circuit which, at the end of a buzz, supplies a buzz reset signal to the output logic unit 36 which in response thereto supplies only the resetting signal to the slave register unit 28 and the choice reset signal to the input logic unit 30 thereby rendering the apparatus ready for another attempt to choose the correct slave shape for the master shape illuminated.

Each time that the output logic unit 36 detects that a wrong choice has been made, the unit 36 supplies a pulse to a mistakes counter and display unit 50 which accordingly counts up and displays one or one more mistake. The same pulse is supplied to a first-in first-out memory unit 51 which has its addressing input terminals coupled by the coupling and encoding assembly 24 to the master and slave register units 25 and 28 so that the coordinate positions of the illuminated master array area and the illuminated slave array area at the time of the wrong choice decision pulse are stored in memory locations of the memory unit 51.

After a pupil has completed a test sheet, ie found the correct choices for all the master shapes, the output logic unit 36 generates, on termination of the last tune, an "end of exercise" signal which causes an "end of exercise" lamp 52, shown in FIG. 2, to be illuminated to draw attention to the test sheet having been completed. The instructor can then review the mistakes made by the pupil by observing the number displayed by the mistakes counter and display unit 50 and pressing the push button review switch 26 for the same number of times as there are mistakes. At each closure of the review switch 26, the review unit 27 supplies a master reset signal to the master register unit 25, and the same signal is supplied to a shift out terminal of the memory unit 51 which in response thereto causes the master array 21 and the slave 22 to illuminate the two respective areas thereof corresponding to the coming with the order of occurrence during the test which corresponds to the order of occurrence of the actuation of the review switch 26 by the instructor.

Each master reset signal is also supplied to the output logic unit 36 which in response to the first master reset signal extinguishes the "end of exercise" lamp 52 and resets the input logic unit 30 if not already reset. Thus at the end of each review, the apparatus is left ready for the pupil to begin a new test sheet or to repeat the sheet reviewed.

The front of the apparatus also includes, as illustrated in FIG. 2, a rotary control knob 53 for varying the volumn of the tune and "raspberry", a rotary control knob 54 for varying the duration of the tune, two adjustable potentiometers 55 and 56 for adjusting respectively the pitch and length of the notes of the tune, two seven segment display numerals 57 and 58 for displaying the number of mistakes, a mains on/off switch 59, a rotary control knob 60 for varying the rate of scanning of the slave array 22 and an array element switch 61 of the array element control 37 for setting to determining whether the arrays 21 and 22 operate with sixteen and twenty-one areas or with four and seven areas as described hereinbefore. A headphone socket 62 is provided adjacent the loudspeaker 32 to allow a headphone set (not shown) to be used instead of the loudspeaker 32, and an input socket 63 is mounted adjacent the loudspeaker 32 to receive a connector plug 64 at the end of the cable of a remote unit 31 for the switches S and P.

The output logic unit 36 includes a switch-on reset circuit which, when the apparatus is switched on by operation of the mains on/off switch 59, clears the memory unit 51, resets the master register unit 25 and causes the slave register unit resetting signal and the input logic unit reset signals to be generated. Thus the apparatus is automatically brought into a ready condition when it is switched on.

Figure 5:
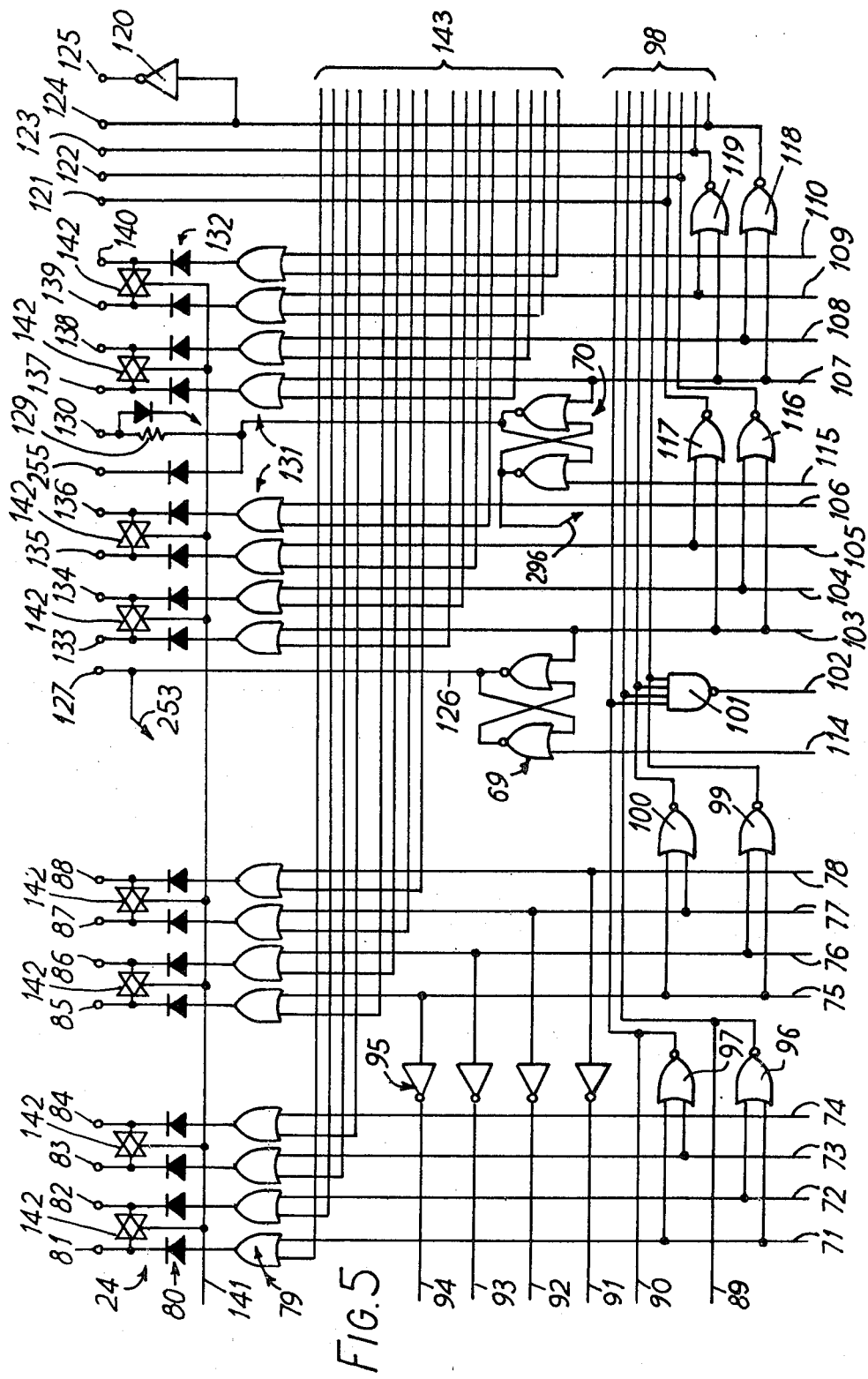
FIGS. 5, 6, 7, 8 and 9 are circuit diagrams of parts of the apparatus of FIGS. 1 and 2.
Figure 6:
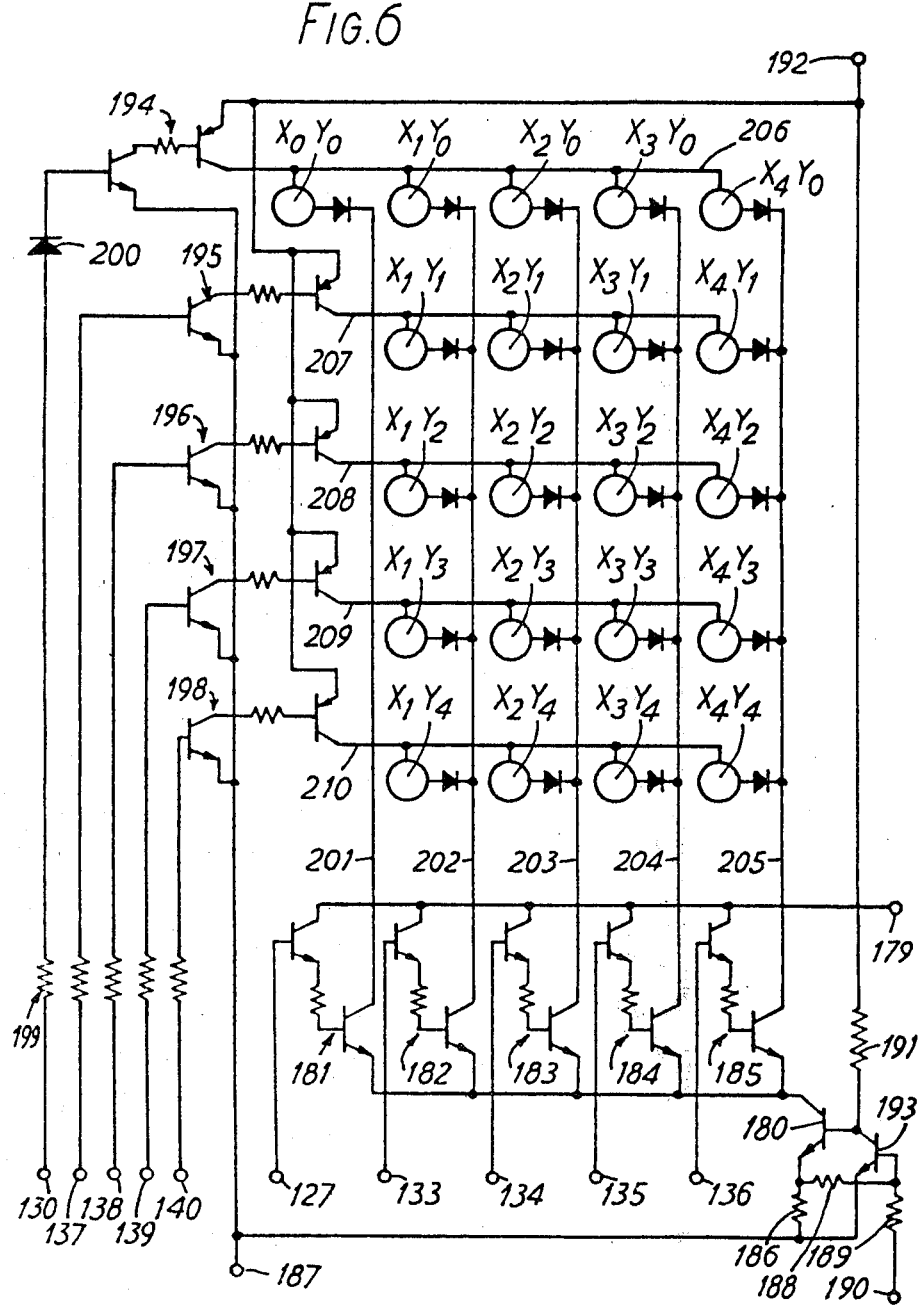
Figure 7:
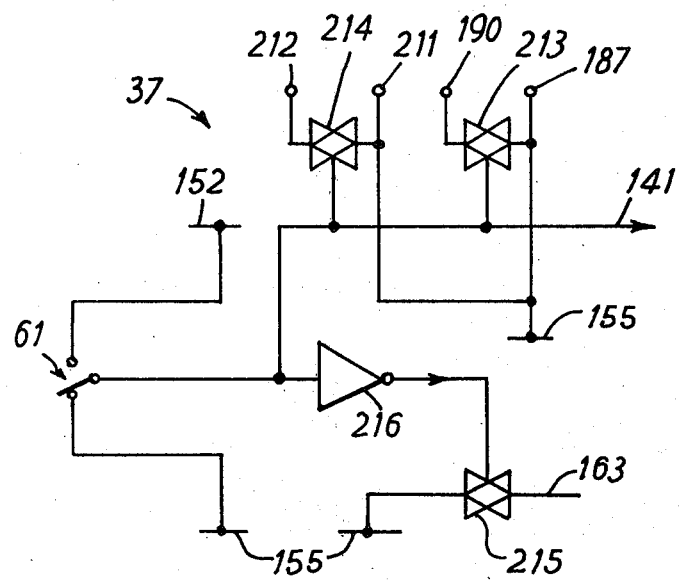
Figure 8:
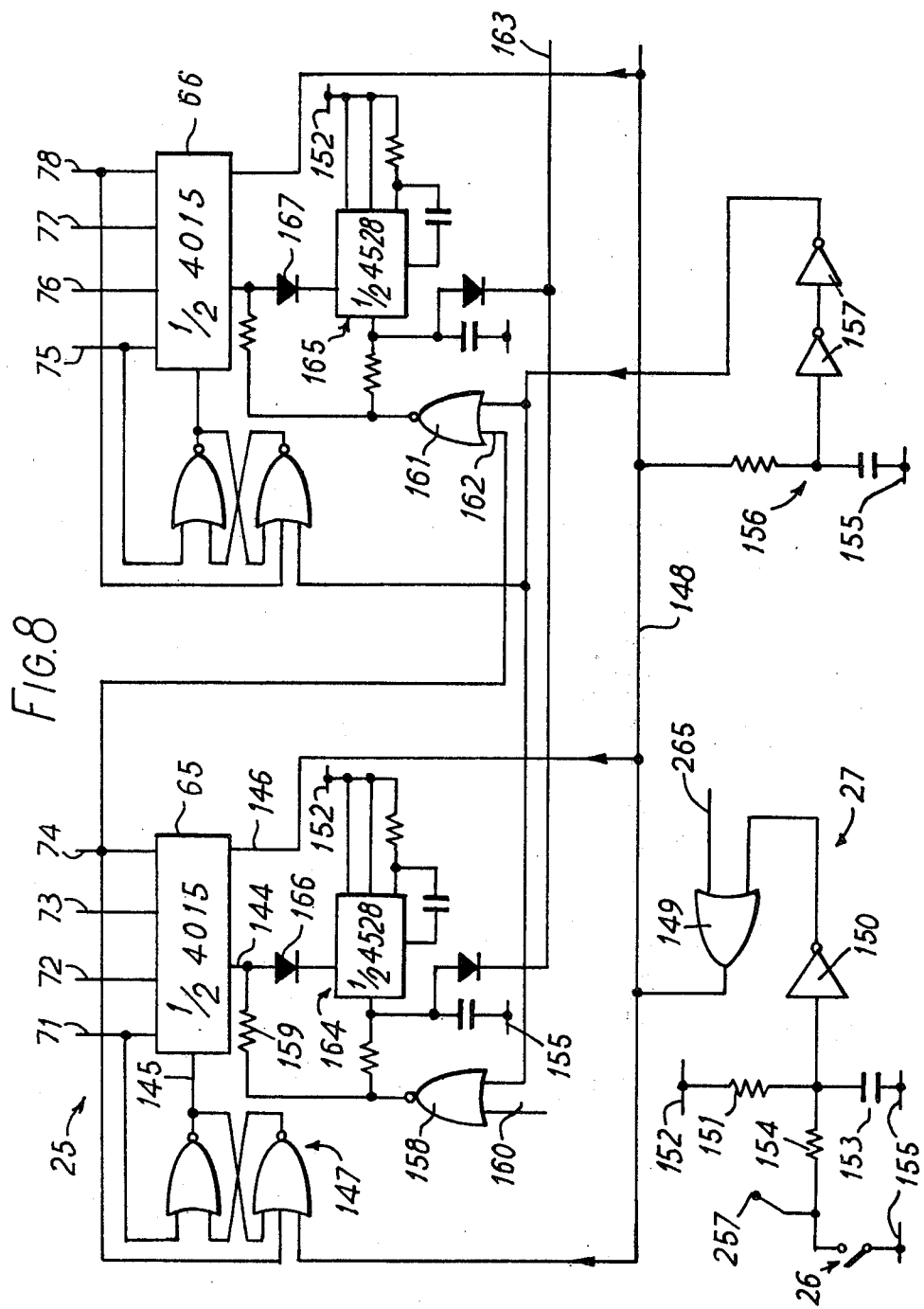
Figure 9:
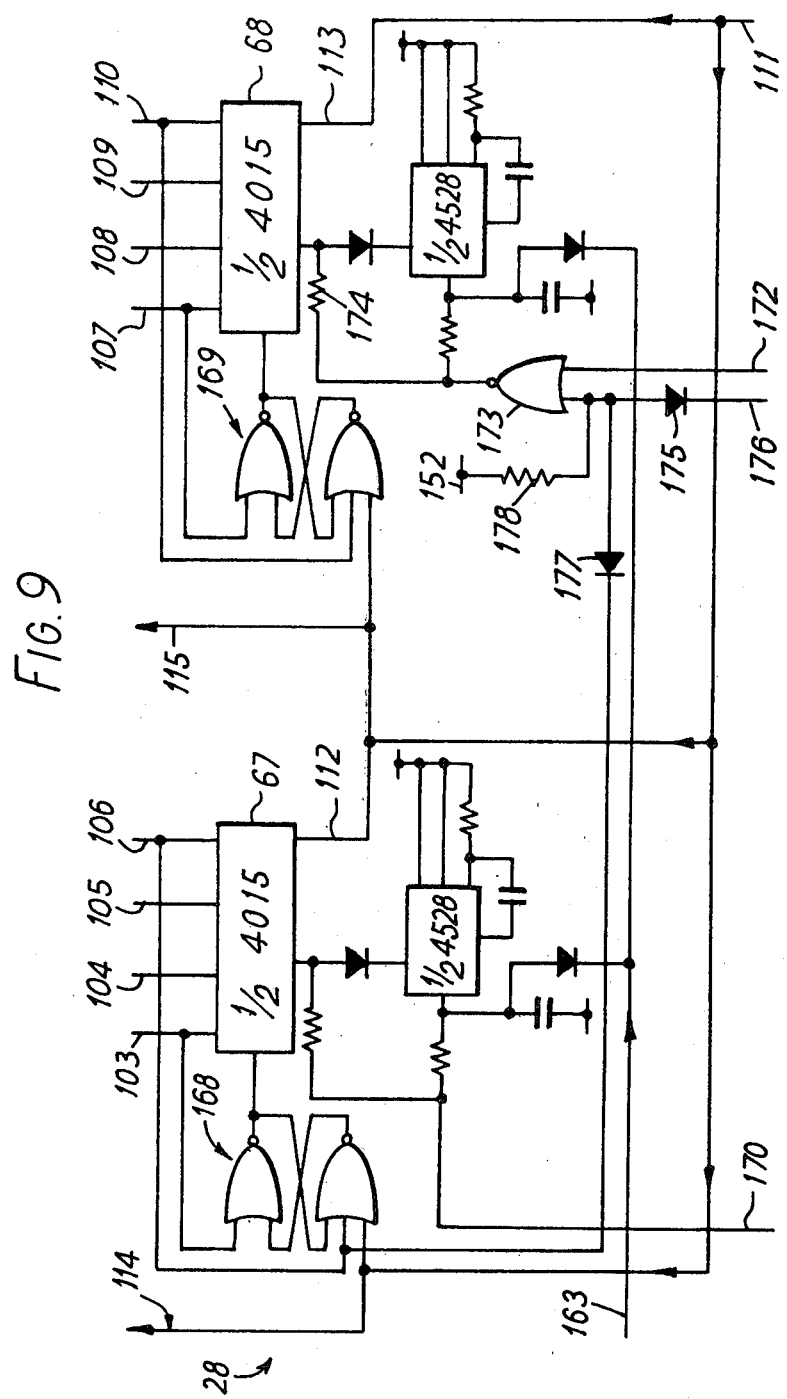
Figure 12:
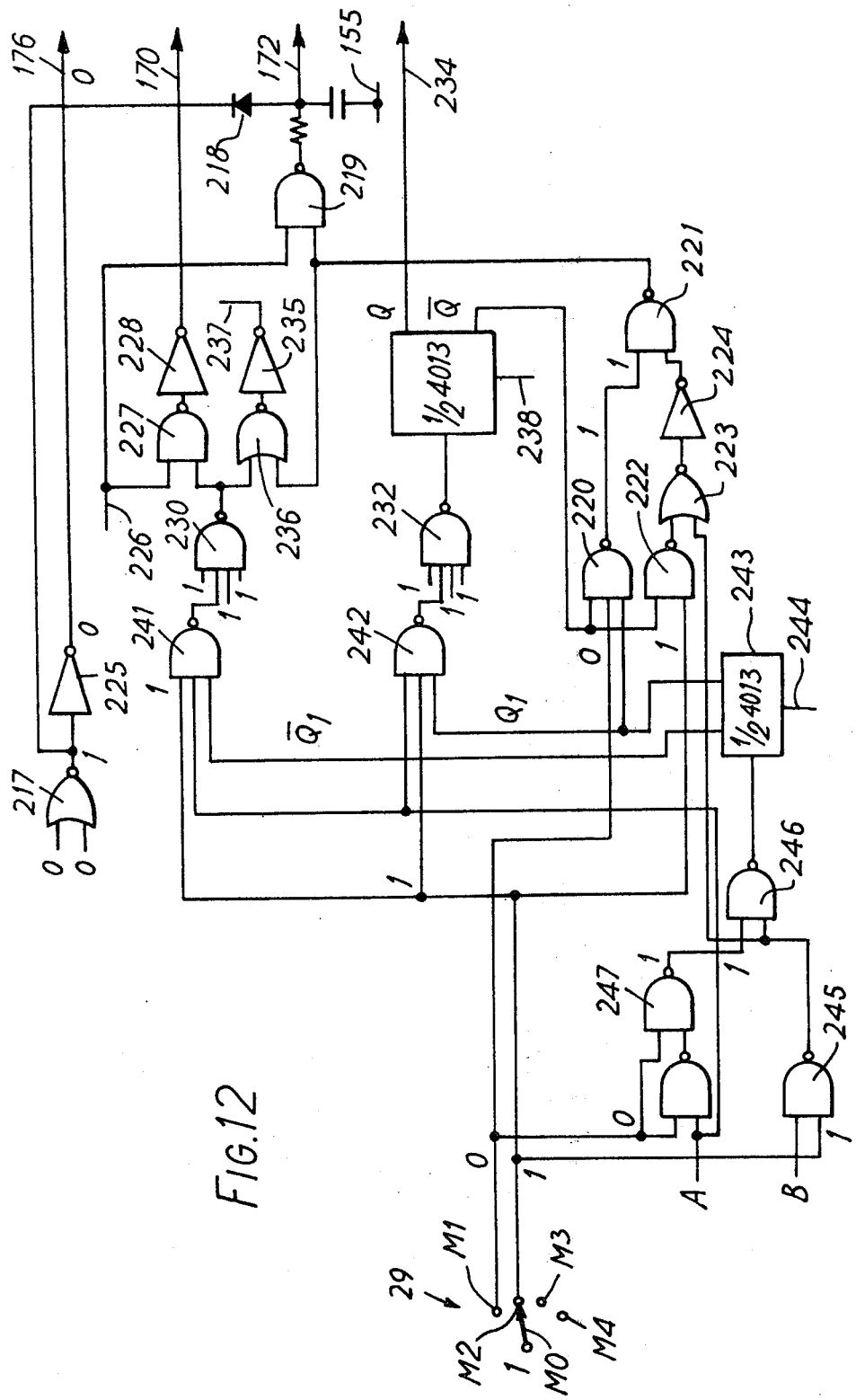
Figure 13:
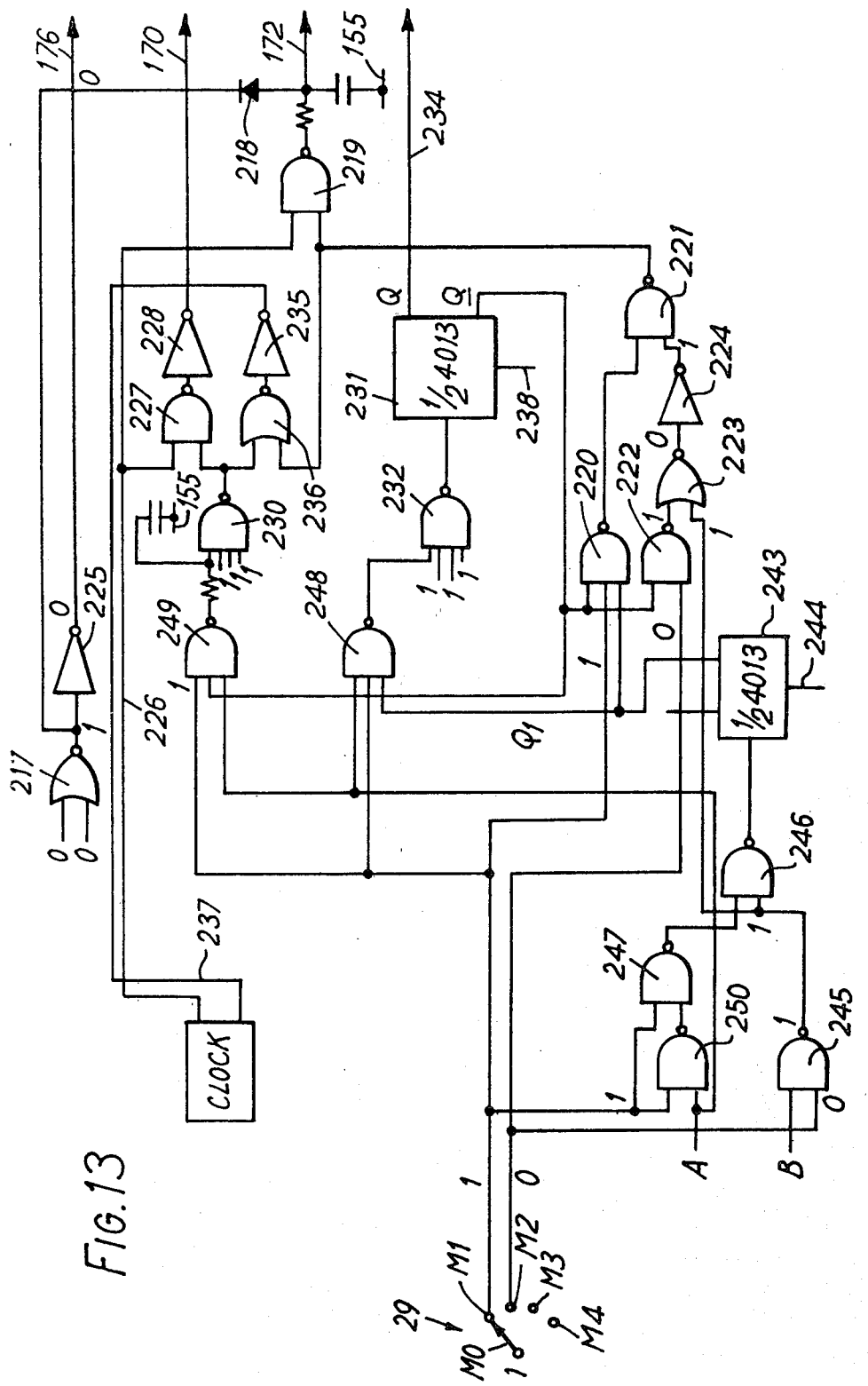
Figure 14:
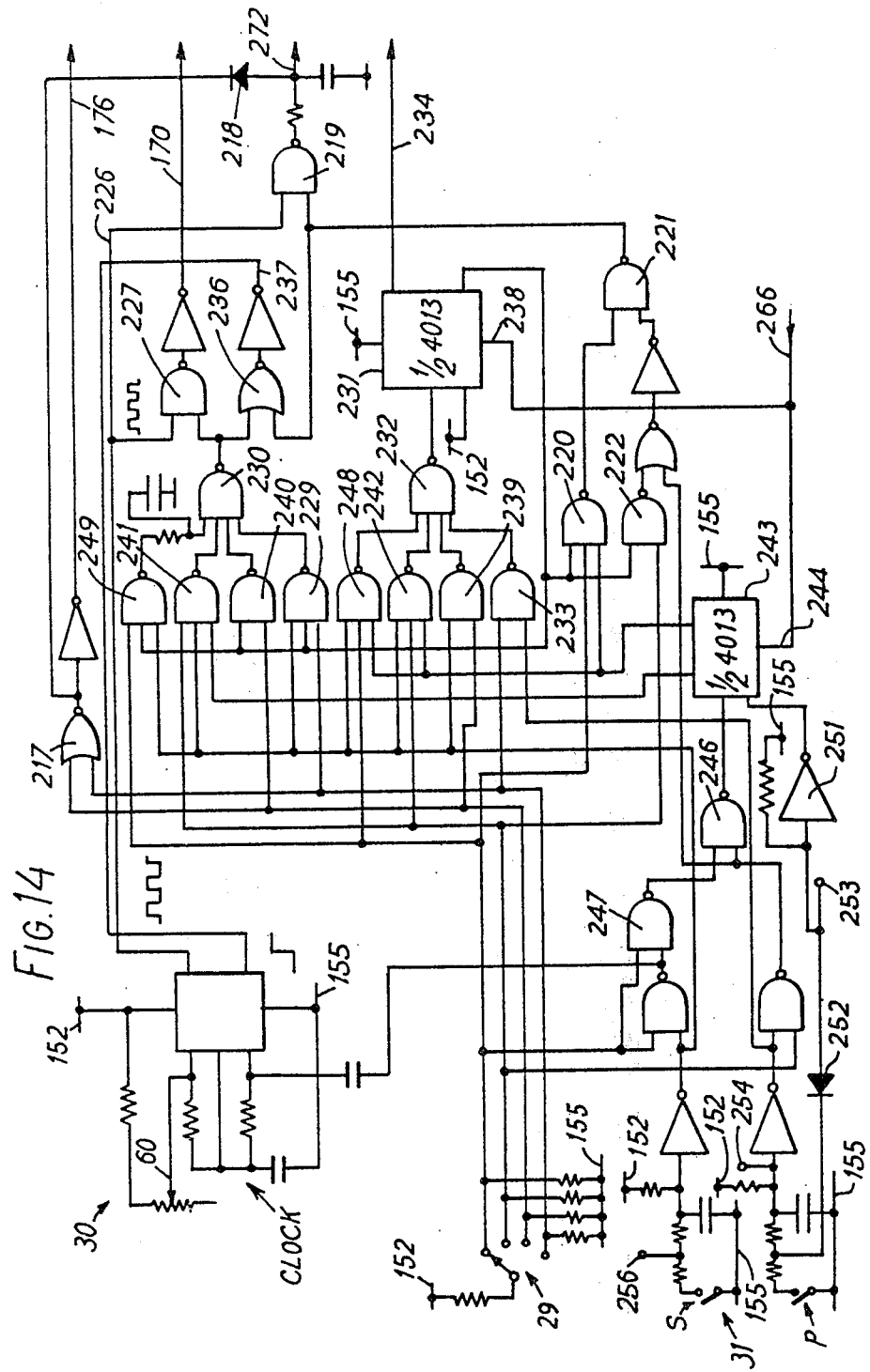
FIGS. 14, 15, 16, 17, 18, 19, and 20 are circuit diagrams of further parts of the apparatus of FIGS. 1 and 2.
Figure 15:
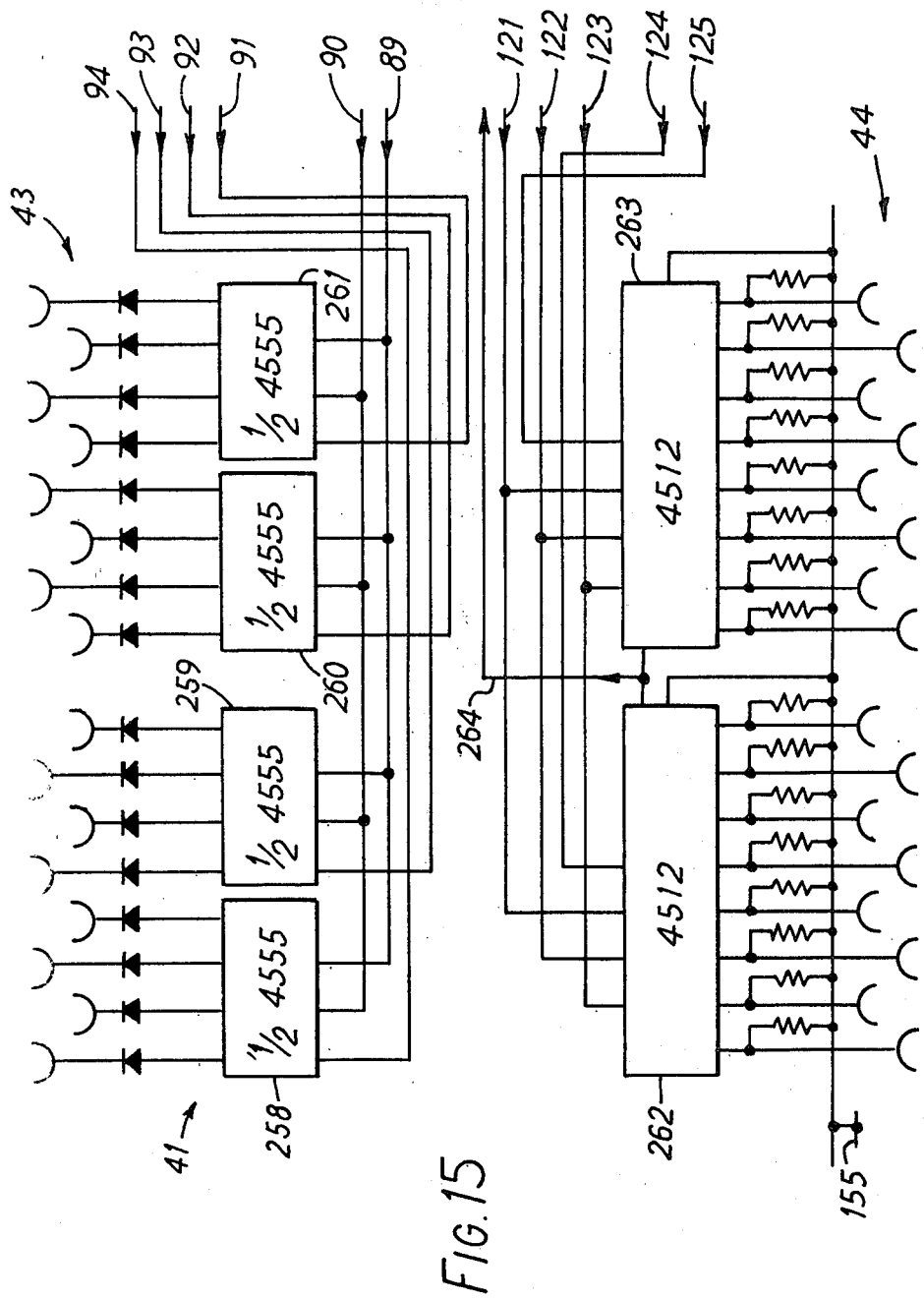
Figure 16:
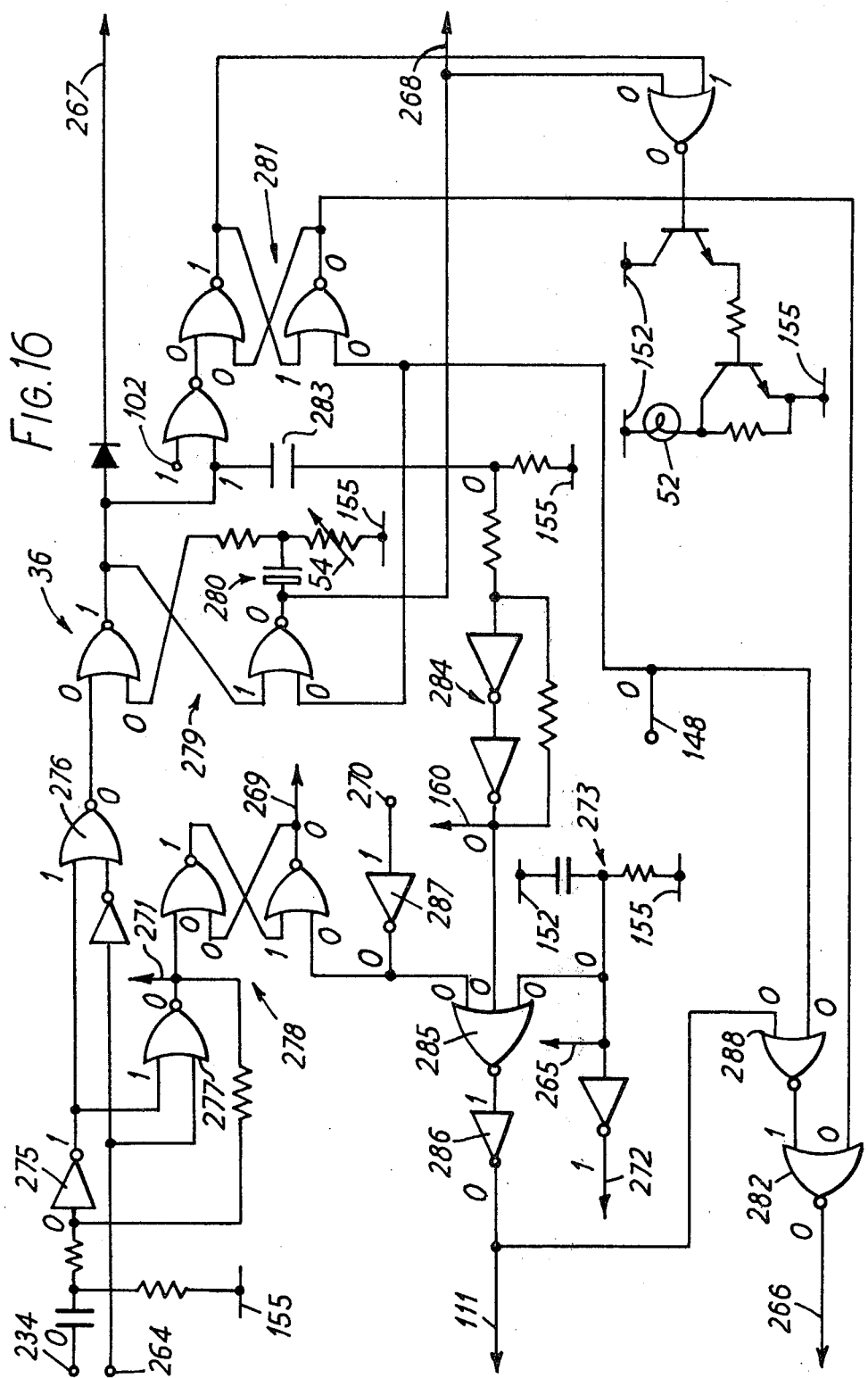
Figure 17:
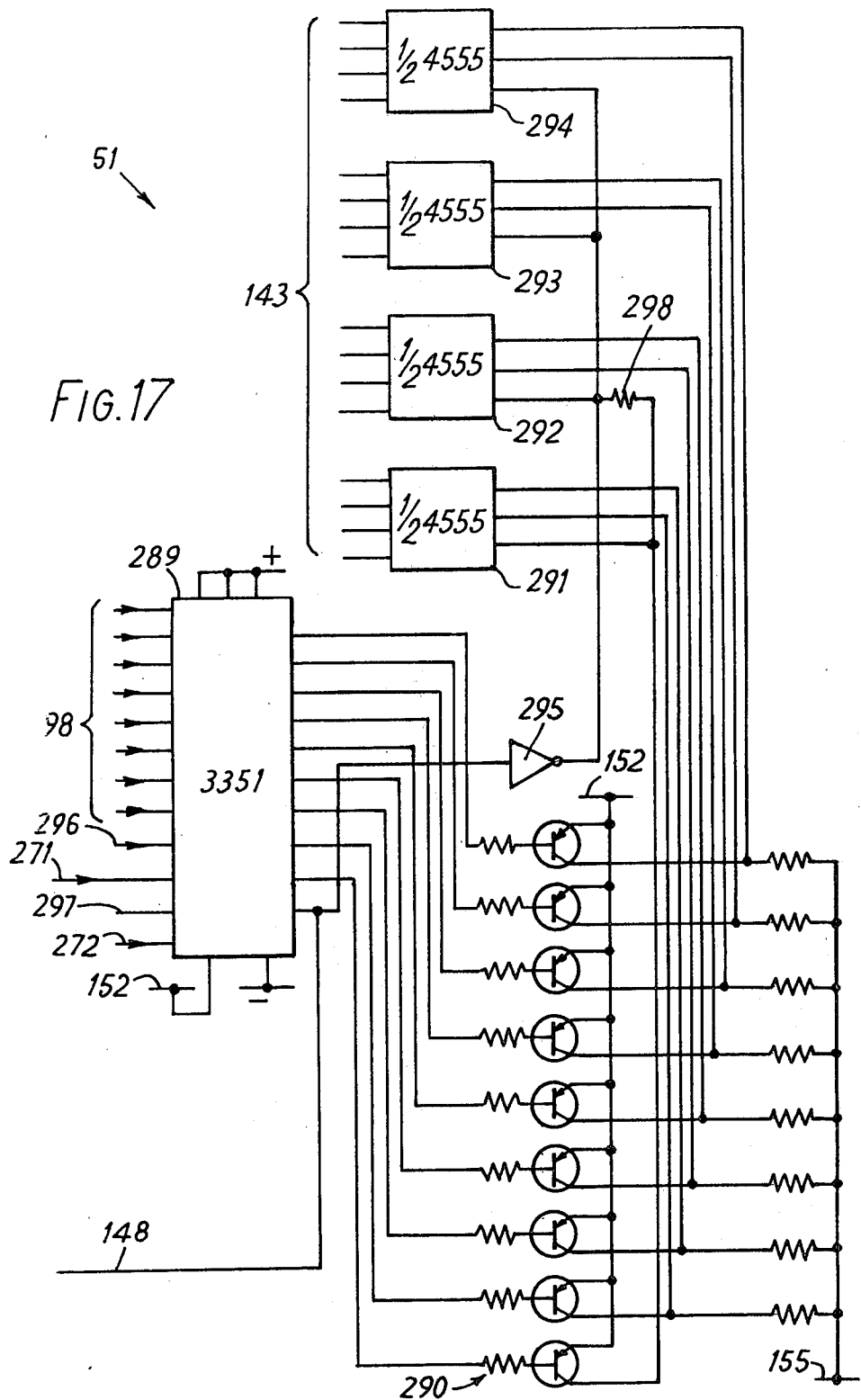
Figure 18:
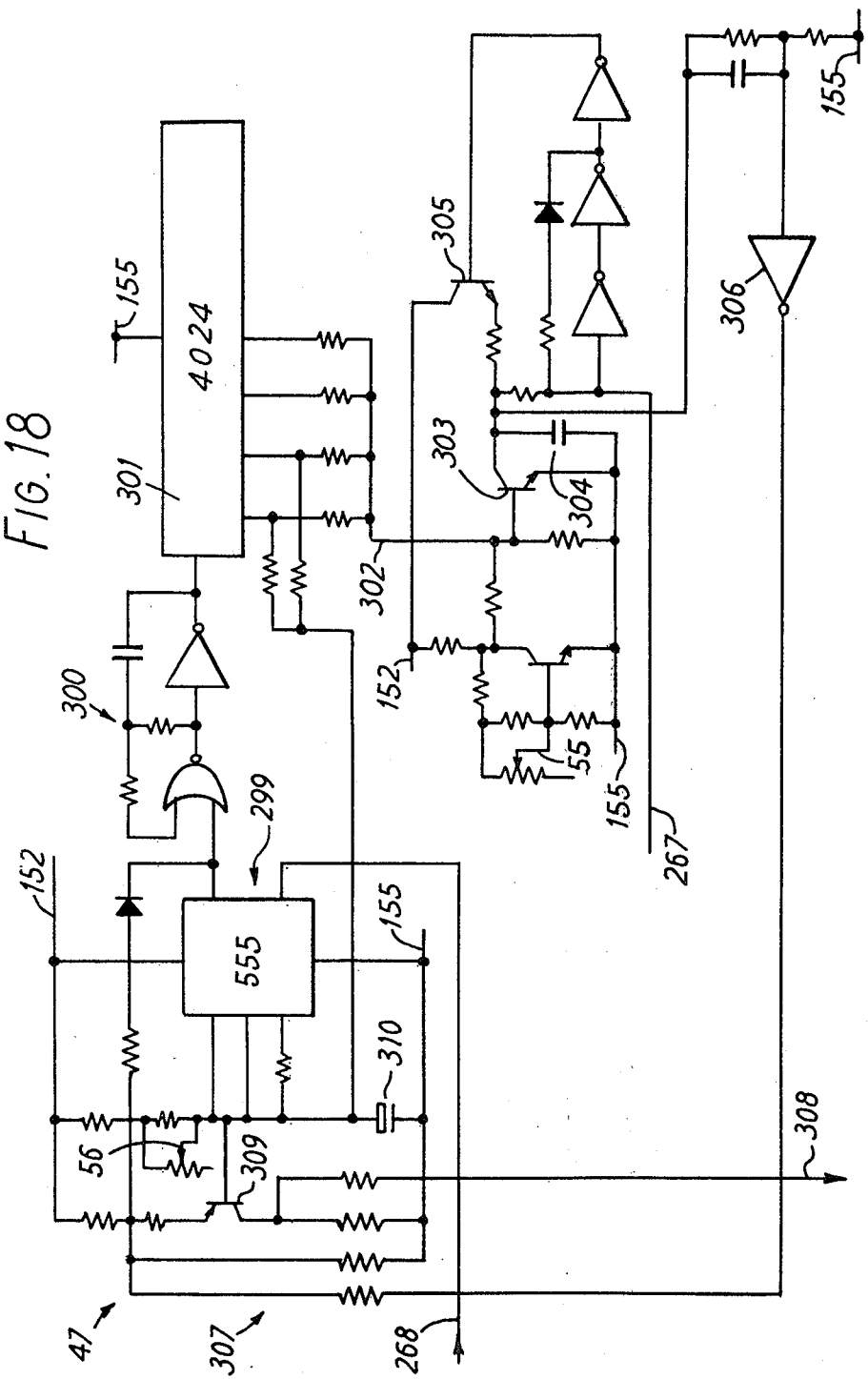
Figure 19:
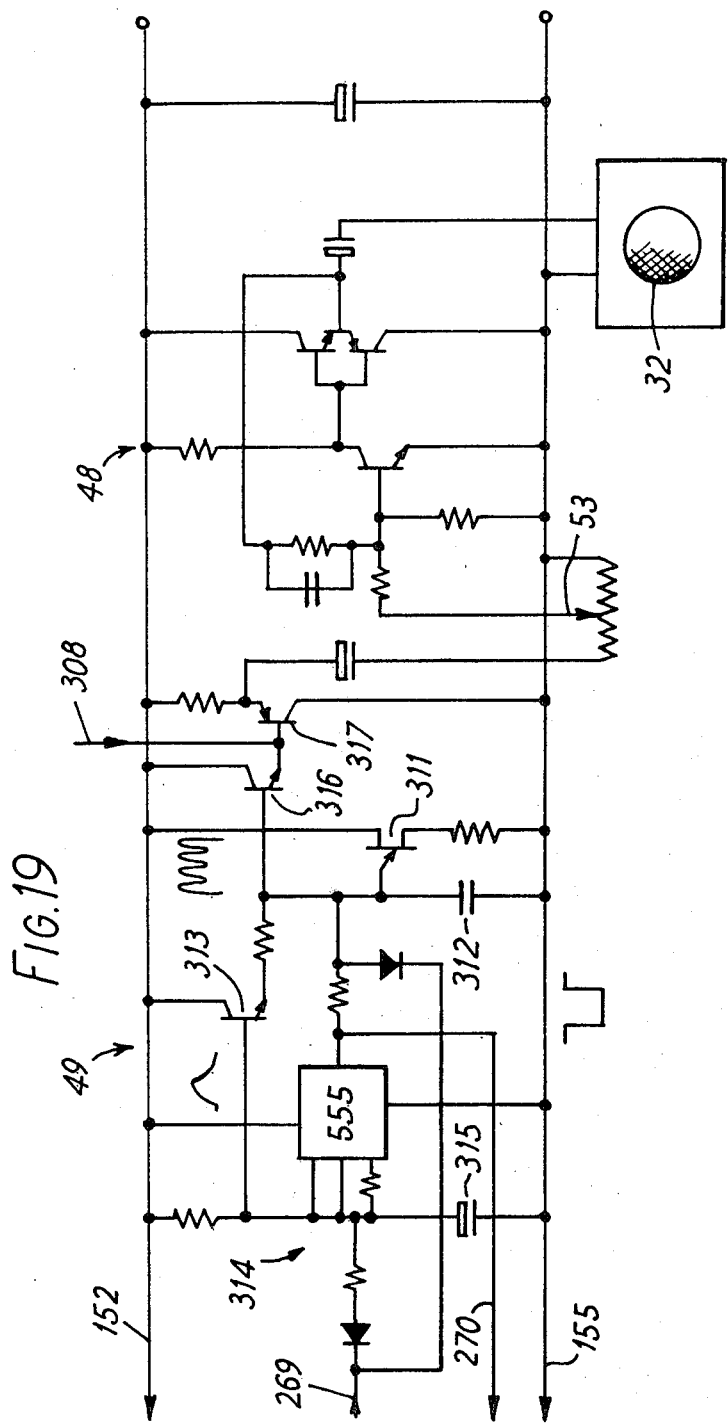
Figure 20:
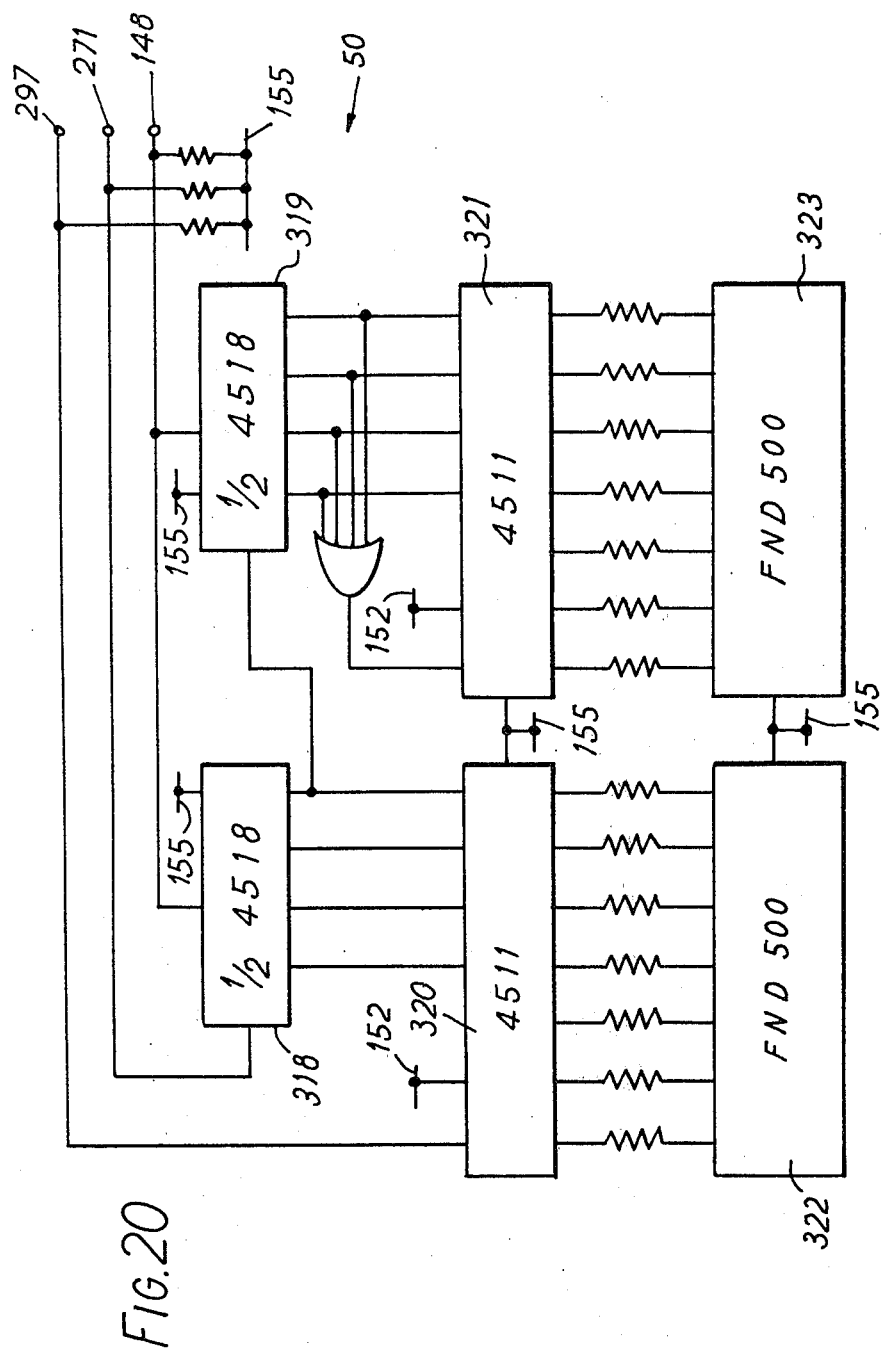

The detailed circuitry of the apparatus of FIGS. 1 and 2 will now be described with reference to FIGS. 4 to 19, FIG. 5 showing the coupling and encoding assembly 24, FIG. 6 showing the circuitry of the slave array 22, FIG. 7 showing the array element control 37, FIG. 8 showing the master register unit 25 and the review unit 27, FIG. 9 showing the slave register unit 28, FIGS. 10, 11, 12 and 13 illustrating the logic of the modes 4, 3, 2 and 1 respectively, FIG. 14 showing the logic input unit 30, the selector switch unit 31, and the mode switch 29, FIG. 15 showing the comparator unit 41, FIG. 16 showing the output logic unit 36, FIG. 17 showing the memory unit 51, FIG. 18 showing the tune generator 47, FIG. 19 showing the buzz generator 49, the amplifier 48 and the loudspeaker 32, and FIG. 20 showing the mistakes counter and display unit 50. In FIGS. 8 to 20, manufacturer's designations for the more complex integrated circuitry (ICs) are indicated within the blocks representing such ICs.

Referring now to FIG. 5, 8 and 9, it will be seen that the master register unit 25 has two shift registers 65 and 66, the slave register unit 28 has two shift registers 67 and 68 and the coupling and encoding assembly 24 includes two NOR gate latches 69 and 70. The shift registers 65 to 68 each have four output terminals corresponding to four stages which comprise the respective shift register. The four output terminals of the shift register 65 are connected to four master column conductors 71, 72, 73 and 74 of the assembly 24. Similarly, the output terminals of the register 66 are connected to four master row conductors 75 to 78 of the assembly 24. Each of the conductors 71 to 78 is connected through a respective OR gate 79 and isolating diode 80 to a respective one of four master array column terminals 81 to 84 or master array row terminals 85 to 88. Six comparator master input terminals 89, 90, 91, 92, 93, and 94 are coupled as shown in FIG. 5 to the master column conductors 71, 72 and 73 and the master row conductors 75 to 78 as shown in FIG. 5. Respective inverters 95 couple the row conductors 75 to 78 to the terminals 94, 93, 92 and 91. Two NOR gates 96 and 97 couple respectively the column conductors 71 and 72 to the terminal 89 and the conductors 71 and 73 to the terminal 90. The NOR gates 96 and 97 also couple the conductors 71, 72 and 73 to two of eight address input terminals 98 of the memory unit 51. Two further NOR gates 99 and 100 couple the row conductors 75, 76 and 77 as shown to two more of the eight memory input terminals 98. The output terminal of each of the four NOR gates 96, 97, 99 and 100 are coupled respectively to four input terminals of a NAND gate 101 which thereby detects the occurence of the illumination of the mast area $C_4R_4$ of the master array 21 and provides a logic 1 signal at its output terminal 102 when this event occurs.

The four output terminals of the slave column or X register 67 are connected respectively to four slave X conductors 103, 104, 105 and 106 of the assembly 24, and the four output terminals of the slave row or Y register 68 are connected respectively to four slave Y conductors 107, 108, 109 and 110. A slave reset input terminal 111 which is connected to respective reset terminals 112 and 113 of the slave registers 67 and 68 is also connected to the respective latch input terminals 114 and 115 of the latches 69 and 70 of the assembly 24. The six slave conductors 103, 104, 105, 107, 108 and 109 are coupled as shown by four NOR gates 116, 117, 118 and 119 to the remaining four memory address input terminals 98 and to four comparator slave input terminals 121, 122, 123 and 124, the NOR gate 118 being also coupled through an inverter 120 to a fifth comparator slave input terminal 25. The latch output terminal 126 of the latch 69 is connected directly to a slave array X-start terminal 127, and the latch output terminal 128 of the latch 70 is coupled through a register 129 to a slave array Y-start terminal 130.

Similarly to the master conductors 71 to 78, the slave conductors 103 to 110 are coupled respectively by OR gates 131 and isolating diodes 132 to four slave array X input terminals 133 to 136, and four slave array Y input terminals 137 to 140.

The sixteen array input terminals 81 to 88 and 133 to 140 are isolated from one another unless a "two-by-two" element control signal is supplied by the array element control 37 to an element control conductor 141 which signal closes eight analogue gates 142 which then connect these terminals in the pairs 81–82, 83–84, 85–86, 87–88, 133–134, 135–136, 137–138 and 139–140.

In addition to being connected to the conductors 71 to 78 and 103 to 110, the OR gates 79 and 131, which are two-input OR gates, each have a second input terminal connected to a respective one of sixteen memory unit output terminals 143. Thus the sixteen OR gates 79 and 131 allow the memory unit 51 to control the arrays 21 and 22.

The operation of the registers 65, 66, 67 and 68 will now be described.

The register 65 has a clock input terminal 144, a D terminal 145 and a reset terminal 146. Application of a reset pulse to the reset terminal 146 resets the four stages of the register to 0000. Subsequent application of clock pulses to the clock input terminal 145 results in shifting of the state of the D terminal 145 stage by stage through the register. The states of the four stages appear as binary signals on the four master column conductors 71 to 74 and the state of the D terminal 145 is determined by the output of a two NOR gate latch 147 connected to be controlled by the binary signals on the first and last column conductors 71 and 74, or by a signal on a master reset conductor 148 which is connected to the reset terminal 146 and to the output terminal of an OR gates 149 forming the output stage of the review unit 27. Normally, when the review switch 26 is open as shown, a logic 0 is present on the master reset conductor 148, the OR gate 149 having logic 0 at both inputs, one of which is connected in the unit 27 to an inverter 150 having a logic 1 as its input as a result of being coupled by a resistor 151 to a positive 12 volt rail 152. To apply a logic 1 to the master reset conductor 148, the review switch 26 is closed, thereby discharging a capacitor 153 through a small resistor 154 which, then in series with the resistor 151, applies logic 0 as the input to the inverter 150, the switch 26 and the capacitor 153 both having one pole connected to a ground rail 155.

With the switch 26 closed, logic 1 on the master reset conductor 148, and 0000 in the register 65, the setting input to to the latch 147 is logic 1. As a result, the output of the latch 147 is logic 1, so that when a first clock pulse is applied to the clock terminal 144, logic 1 is shifted into the register 65 and appears on the first conductor 71. Logic 1 on the conductor 71 resets the latch 147 so that logic 0 appears at the D terminal 145. The switch 26 is released so that logic 0 reappears on the conductor 148. Consequently, second, third and fourth clock pulses supplied to the clock terminal 144 result in logic 0 appear in the first stage, then the second stage, and then the third stage of the register 65 as logic 1 moves from the first to the fourth stages. Thus the column conductors 71 to 74 have respectively the binary signals 0000, 1000, 0100, 0010 and 0001. The appearance of logic 1 on the last conductor 74 with logic 0 on the first conductor 71 sets the latch 147 again so that logic 1 is applied to the D input 145. Thus as the next clock pulse after the state 0001 is reached, the contents of the register 65 become 1000, and subsequent clock pulses continue the cycle through 0100, 0010, 0001, 1000, and so on until the register 65 is reset to 0000 by logic 1 appearing on the master reset conductor 148.

A first clock pulse is supplied automatically as a result of closure of the review switch 26, since the logic 1 which then appears on the master reset conductor 148 is coupled, with delay by a resistor-capacitor combination 156 and shaping by two series Schmitt inverters 157, through a NOR gate 158 and a resistor 159 to the clock terminal 144. Subsequent clock pulses are supplied to the NOR gate 158 at master advance input terminal 160 of the NOR gate 158 by the output logic unit 36.

The register 66 operates in the same way as the register 65 except that the NOR gate 161 corresponding to the NOR gate 160 has its advance input terminal 162 connected to the last column conductor 74 so that logic 1 in the register 66 shifts only one stage along for each complete cycle of the register 65. Thus together the two registers 65 and 66 provide a predetermined scanning sequence in which logic 1 appears at the array input terminals 81, 82, 83 and 84 in that order while logic 1 is at the terminal 85, then again at 81 to 84 with logic 1 at 86, then with logic 1 at 87 and finally with logic 1 at 88.

When the said two-by-two element control signals appears at the element control conductor 141, a corresponding signal also appears at a clock control conductor 163 of the master register unit 25. This signal unclamps respective monostable circuits 164 and 165, each consisting of half a 4528 IC with suitable resistors and capacitors as shown, coupled to the clock terminals of the registers 65 and 66 by respective diodes 166 and 167. As a result, after each clock pulse supplied to the respective NOR gate 158 or 161, a further clock pulse is supplied to the respective clock terminals of the register 65 or 66 by the monostable circuit 164 or 165, and logic 1 shifts two stages through the respective register for each clock pulse supplied to the NOR gate 158 or 161. This ensures that tune generation by the tune generator 47 is followed by an advance of the master array 21 when the array is of four elements only.

As will be seen from FIG. 9, the operation of each of the slave registers 67 and 68 is substantially the same as the operation of the master register 65. The slave reset terminal 111 is connected to the setting terminals of respective latches 168 and 169 at the D terminals of the registers 67 and 68. An X-clock input terminal 170 is coupled through a resistor 171 to the clock terminal of the register 67, and a Y-clock input terminal 172 is coupled through a NOR gate 173 and a resistor 174 to the clock terminal of the register 68.

The second input terminal of the NOR gate 173 is coupled by a diode 175 to a mode control input terminal 176 and by a diode 177 to the last X conductor 106. The diodes 175 and 177 are so arranged that when the diode 175 conducts, which it does as the result of a logic 0 applied in modes 1 and 2 to the mode control input terminal 176, that input terminal of the NOR gate 173 to which the diodes 175 and 177 are connected is held at logic 0 whatever logic signal is present at the X conductor 106, and that when the diode 175 is not conducting, as a result of a logic 1 applied to modes 3 and 4 to the mode control input terminal 176, that input terminal of the NOR gate 173 is at logic 0 whenever there is logic 0 on the conductor 106 and at logic 1 whenever there is logic 1 on the conductor 106, the diode 177 in the latter case being non-conducting and a positive twelve volts being applied from the positive rail 152 through a resistor 178 to the said input terminal of the gate 173. Hence, it will be seen, when there is logic 1 at the mode control input terminal 176, the register 68 is supplied clock pulses by the last stage of the register 67 through the coupling of the conductor 106 by the diode 177 to the NOR gate 173 and the two slave registers 67 and 68 operate in the same manner as described with reference to the master registers 65 and 66, with the X register 67 driving the Y register 68.

When a logic 0 is present at the mode control input terminal 176, the NOR gate 173 is isolated from the X register 65 and clock pulses applied to the Y-clock input terminal 172 control the state of the Y register 68.

Referring to FIG. 5, it will be seen that the latch 69 is controlled by inputs from the slave reset terminal 111 and the first X conductor 103 in the same way as the latch 168 is controlled by these inputs. Similarly, the latch 70 is controlled by the signals at the reset terminal 111 and the first Y conductor 107. As a result, each time that the slave registers 67 and 68 are reset, a logic 1 appears at the slave start terminals 127 and 130. This logic 1 is in each case replaced by a logic 0 as soon as the first clock pulse applied to the register 67 or 68 changes the signal on the respective first conductor 103 or 107 to logic 1 and thereby resets the latch 69 or 70. In the absence of a further reset logic 1 on the terminal 114 or 115, the respective latch 69 or 70 remains in a state providing a logic 1 at the terminal 127 or 130.

FIG. 6 shows the circuitry of the slave array 22 connected to the terminals 127, 133 to 136, 130 and 137 to 140. In this circuitry, twenty one light sources are identified by the references of the array as shown in FIG. 2. The X terminals 127 and 133 to 136 are connected respectively to control five transistor switches 181 to 185 connected between a positive twelve volt terminal 179 and a current controlling transistor 180. The transistor 180 has a collector connected to the switches 181 to 185, an emitter coupled through a resistor 186 to a ground terminal 187 and through two resistors 188 and 189 in series to a current control input terminal 190, and a base coupled through a resistor 191 to a positive twenty four volt terminal 192, and through a further transistor 193 to the ground terminal 187.

The base of the further transistor 193 is coupled by the resistor 189 to the current control terminal 190. This terminal 190 is either grounded or is floating so that the base of the further transistor 193 is at the voltage of the emitter of the current control transistor 180. When the terminal 190 is grounded, the impedance of the transistor 193 is high and a high forward bias is applied to the base-emitter junction of the transistor 180 which therefore presents a low impedance to the switches 181 to 185. When the terminal 191 is floating, the impedance of the transistor 193 is low and a small forward bias is applied to the base-emitter junction of the transistor 180 which therefore presents a high impedance to the switches 181 to 185. The low impedance state of the current control transistor 180 is established when the array 22 is operated as a seven element array, as described hereinbefore, and the high impedance state of the current control transistor 180 is established when the array 22 is operated as a twenty-one element array.

The Y terminals 130 and 137 to 140 are respectively connected to control five further transistor switches 194 to 198 connected between the terminals 192 and 187 as shown.

The five transistor switches 181 to 185 respectively control five slave column conductors 201 to 205 coupled by diodes poled as shown to the twenty one light sources $X_0Y_0$ to $X_4Y_4$, and the five transistor switches 194 to 198 respectively control five slave row conductors 206 to 210 connected directly to these twenty one light sources as shown.

When a logic 1 is applied to the terminal 130, current flows through a respective one of five resistors 199 and a diode 200 to the switch 194 which then closes and thereby applies a positive voltage to the row conductor 206. If then a logic 1 is applied to the terminal 127, the switch 181 closes and applied a low voltage to the column conductor 201. The diode of the light source $X_0Y_0$ is thus biased to conduct and the light source $X_0Y_0$ is energised. Similarly, any one of the other twenty one light sources $X_1Y_0$ to $X_4Y_4$ can be energised by application of logic 1 to the appropriate pair of terminals selected from the nine terminals 130 and 133 to 140.

When the analogue gates 142 of the assembly 24 are closed, logic 1 appears at pairs of the terminals 133 to 140 as described hereinbefore, so that the light sources $X_1Y_1$ to $X_4X_4$ operate in the four groups of four as described hereinbefore.

The circuitry of the master array 21 differs from that of FIG. 6 only in the absence of items corresponding to components 127, 130, 191, 194, 200, 201, 206 and the $Y_0$ row of light sources and their diodes.

FIG. 1 shows the circuit of the array element control 37 which, it will be seen, is connected to the terminals 187 and 190 of the slave array circuit of FIG. 6 and to the two corresponding terminals 211 and 212 of the master array circuit (not shown). The current control terminals 190 and 212 can be coupled to the ground rail 155 by closing two analogue gates 213 and 214 which, in common with the analogue gates 142, are controlled by the switch 61 which connects the conductor 141 to the positive rail 152 or to the ground 155 depending on its state. FIG. 7 shows the siwtch 61 connecting the conductor 141 to the ground rail 155 so that the analogue gates 142 and 213 and 214 are all open. A further analogue gate 215 is controlled in the opposite manner by the switch 61 to which it is coupled by an inverter 215. Thus the conductor 163 to which the gate 215 is connected is grounded when the gates 213 and 214 and 142 are open, and is floating when they are closed.

Figure 10:
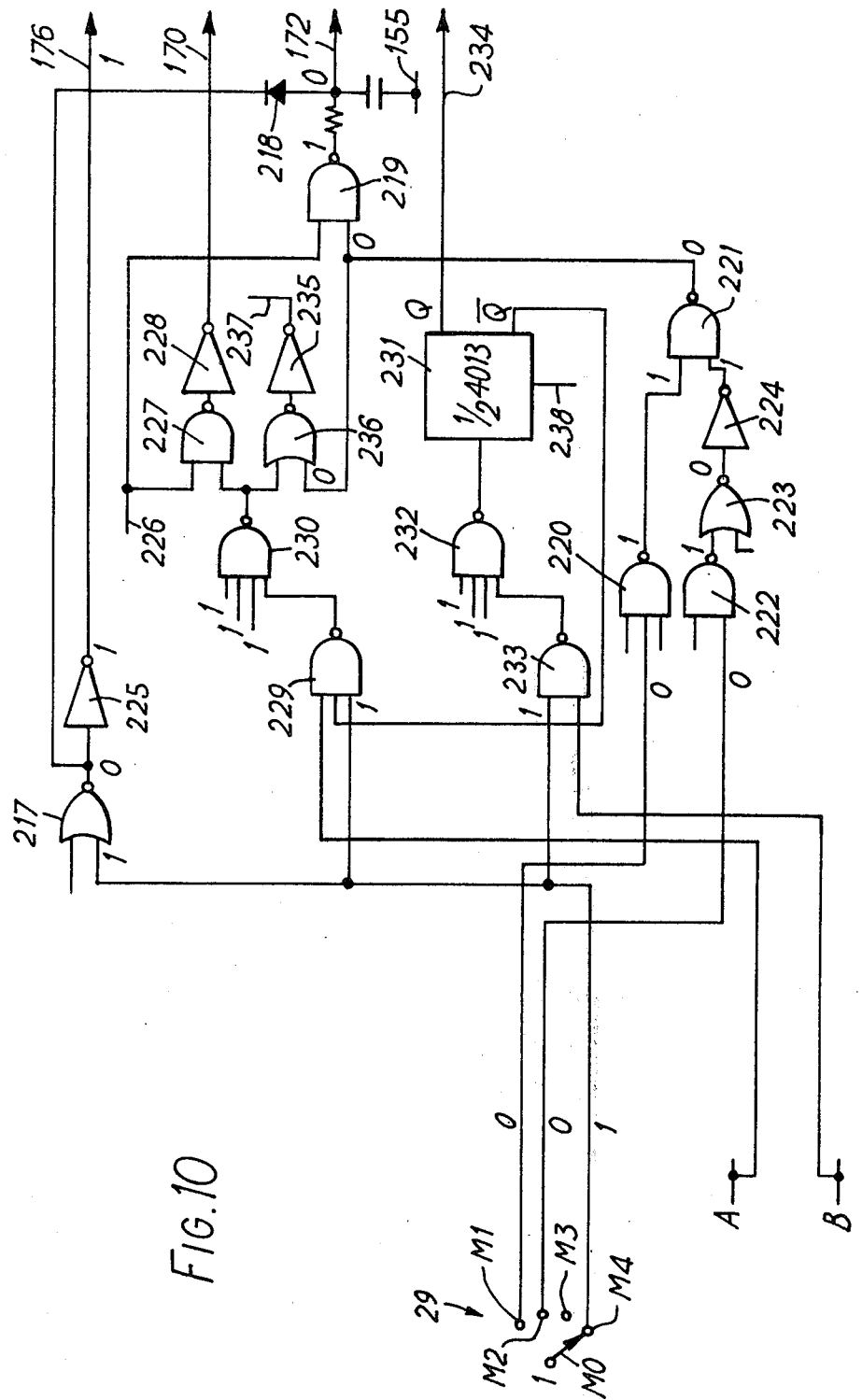
FIGS. 10, 11, 12, and 13 are diagrams of mode logic of the apparatus of FIGS. 1 and 2.

FIG. 10 shows the logic effective in the input logic unit 30 in mode 4, and logic valves 1 and 0 are indicated where established in the mode. Signals applied by the switches S and P are represented by A and B respectively and may each be either logic 0, corresponding to the respective switch being open, or logic 1 corresponding to the respective switch being closed. The mode switch 29 has a movable contact M0 at logic 1 which can be set in contact with any one of four terminals M1, M2, M3 and M4 which are used respectively in the first to fourth modes. Thus in FIG. 10 the contact M0 applies logic 1 to the mode 4 contact M4. Those three contacts, in this mode M1, M2 and M3, which are not in contact with the movable contact M0 are at logic 0. Logic 1 on M4 establishes logic 0 at the Y clock terminal 172 through a NOR gate 217 and a diode 218. Logic 0 at the contacts M1 and M2 block a Y clock pulse NAND gate 219 by establishing logic 0 as one of its inputs through, from M1, a NAND gate 220 and a NAND gate 221, and, from M2, a NAND gate 222, a NOR gate 223, an inverter 224 and the NAND gate 221.

A logic 1 signal which renders the diode 175 of FIG. 9 non-conducting is provided at the mode control terminal 176 by an inverter 225 at the output of the NOR gate 217.

With $A=1$ and $B=0$, clock pulses on a clock line 226 are supplied through a NAND gate 227 and an inverter 228 to the X clock terminal 170, the NAND gate 227 being opened by a logic 1 established by $A=1$ through NAND gates 229 and 230, the gate 229 being held open by logic L from $A=1$ and from $Q=1$ from a bistable 231. The gate 229 closes when $A=0$ and the gate 227 closes in response.

To indicate a choice, the switch P is closed to give $B=1$ which results in a positive going edge being applied to the bistable 231 by a NAND gate 232 controlled by a NAND gate 233 with inputs $M4=1$ and $B=1$. This positive going edge sets the bistable 231 so that $Q=0$ and $\overline{Q}=0$ for this bistable. Consequently the NAND gate 229 closes and the X clock pulse terminal 170 is set at logic 0. The output $\overline{Q}=1$ of the bistable 231 is applied to a "selection complete" terminal 234 which is connected to the output logic unit 36. The logic 0 which appears at the output of the NAND gate 230 also changes the output of an inverter 235 controlled by a NOR gate 236 with inputs from the gates 230 and 221 from logic 1 to logic 0. The logic 0 output of the inverter 235 is applied to a clock pulse enable terminal 237 to inhibit clock pulses at the line 226. A resetting signal supplied by the output logic unit 36 to the input logic unit 30 is applied to a reset terminal 228 of the bistable 231 to re-establish $Q=0$ and $\overline{Q}=1$.

Figure 11:
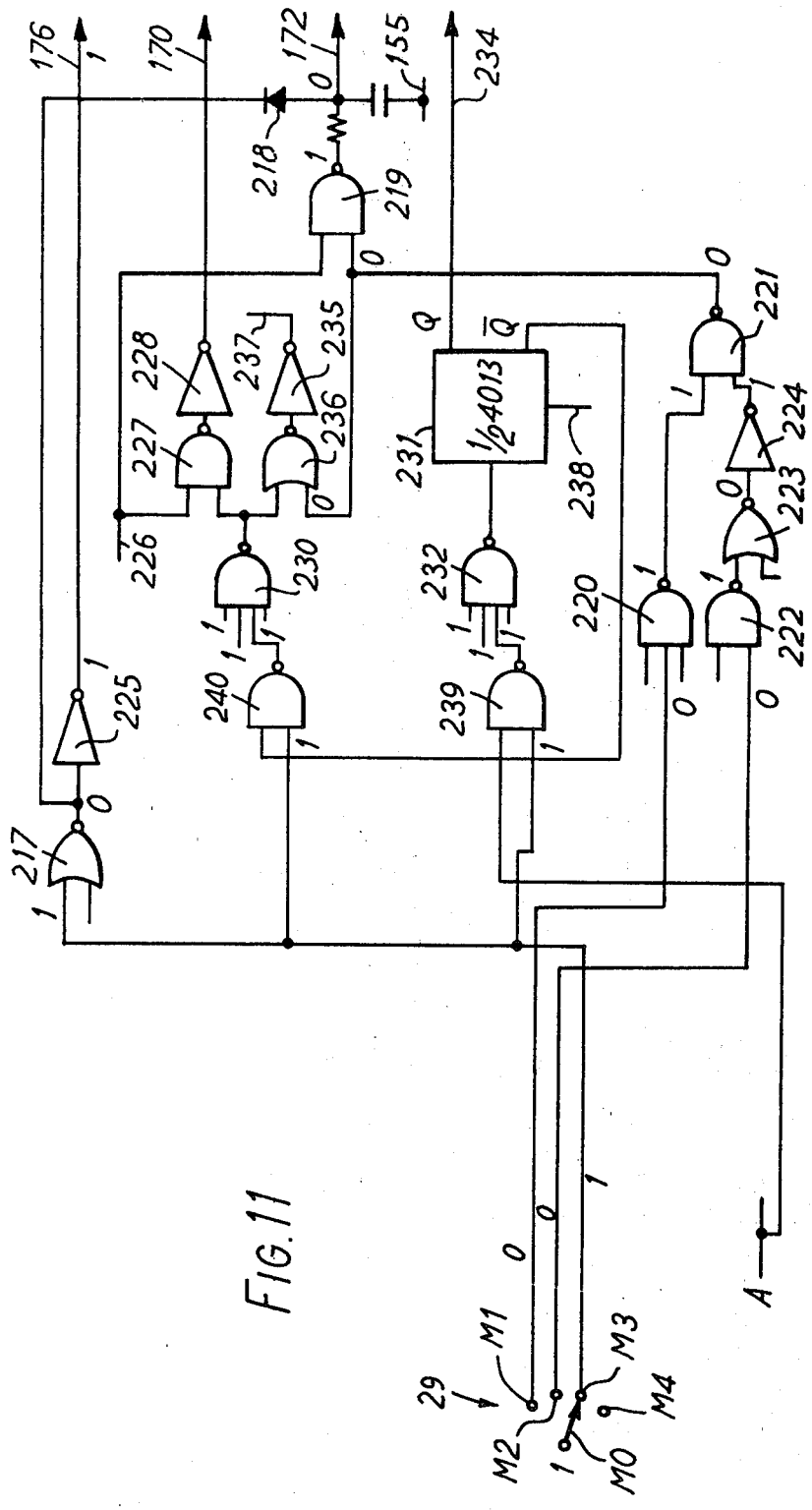

FIG. 11 shows the logic of mode 3 which is similar to that of mode 4 but utilises a NAND gate 239 to control the gate 232 and hence the bistable 231 in accordance with the value of B, and a NAND gate 240 to control the gate 230. It will be seen that clock pulses pass from the rail 226 to the terminal 170 until P is closed to make $B=1$ whereupon $\overline{Q}=0$ and the gate 240 closes thereby closing the gate 227.

FIG. 12 shows the logic of mode 2 in which logic 1 on M2 is applied to a NAND gate 241 which controls the gate 230, and to a NAND gate 242 which controls the gate 232. Logic 0 on M1 is applied to the gate 220 to open the gate 221.

At the start of mode 2, a further bistable circuit 243 is in a reset condition in which its outputs are $Q_1=0$ and $\overline{Q}=1$ as a result of an input logic resetting signal having been applied to its reset terminal 244. Consequently the NAND gate 241 is open as a result of inputs $M2=1$ and $\overline{Q_1}=1$, and the NAND gate 242 is closed as a result of inputs $M2=1$ and $Q_1=0$. Closure of the gate 242 ensures that mode 2 starts with logic 0 applied by the gate 232 to the bistable 231.

If switch 5 is now closed so that $A=1$, gates 241 and 230 open gate 227 and clock pulses appear on the X clock terminal 170. The switch S can be opened and closed as desired to supply clock pulses to the terminal 170 at this stage in the mode provided $B=0$. If switch P is now closed so that $B=1$, a NAND gate 245 opened by $M2=1$ now applies logic 0 to gates 241 and 242, thereby stopping the flow of clock pulses to the terminal 170 and ensuring, for a reason which will appear, that the gate 242 remains closed. The apperance of the logic 0 supplied by the gate 245 causes the further istable 243 to be set, the output of a NAND gate 246 controlled by the gate 245 and a NAND gate 247 with an output logic 1 fixed by $M1=0$ being switched from logic 0 to logic 1 and thereby supplying a positive going edge to set the bistable 243. Hence when $B=1$, $Q_1=1$ and $\overline{Q_1}=0$. Gate 241 is therefore now held closed by $Q_1=0$ and subsequent closure of switch S cannot cause further clock pulses to appear at the X terminal 170, and gate 242 is primed ready by $Q_1=1$ to open when $A=1$ next occurs.

Logic 0 at the output of the gate 245 also results in the gate 219 being opened as will be seen by considering the conditions of the gates 220, 222, 223 and 221 when B changes from $B=0$ to $B=1$ and $Q_1$ changes from $Q_1=0$ to $Q_1=1$, with $\overline{Q}=1$.

When gate 219 is open, clock pulses from the clock pulse line 226 are passes inverted through the gate 217 to the Y clock terminal 172, the diode 218 being non-conducting as a result of $M3=0$ and $M4=0$ applied to the NOR gate 217.

Switch P can be opened and closed as desired at this stage of mode 2 provided $A=0$.

When next $A=1$, the output of gate 242 becomes logic 0, and the output of the gate 232 switches from logic 0 to logic 1, thereby setting the bistable 231 so that as a result $Q=1$ and $\overline{Q}=0$. Thus gates 220, 222 and 219 are closed, no more clock pulses can reach Y terminal 172, and the "selection complete" signal $Q=1$ appears at the terminal 234.

FIG. 13 shows the logic of mode 1 which is similar to that of mode 2 except that A controls all stages of the mode and B has no effect being blocked by the gate 245 which receives $M2=0$ as an input. Gate 221 is nevertheless open since $M2=0$ establishes logic 1 at the output of the inverter 224 through gates 245 and 223, and also through gate 222. Gate 221 is then ready to apply logic 1 to open the gate 219 when $Q_1$ switches from $Q_1=0$ to $Q_1=1$. Initially, as in mode 2, $Q_1=0$. With $Q_1=0$, a NAND gate 248 which controls the bistable 231 through the gate 232 establishes logic 0 at the output of the gate 232. A NAND gate 249 which controls the gate 227 through the gate 230 is then held open by $M1=1$ and $Q=1$ and is controlled by A. With $A=0$, gate 227 is closed. Closing switch S to give $A=1$ opens gate 227 and clock pulses appear at the X clock terminal 170 until S is closed again. A is also supplied to a NAND gate 250 which in this mode controls the gate 247, both gates 247 and 250 being open as a result of $M1=1$. When initially $A=0$, gate 247 applies logic 0 to gate 246 which consequently applied logic 1 to the bistable 243. The bistable 243 is not affected since it only responds to positive going edges. When A switches from $A=0$ to $A=1$, the outputs of the gates 250 and 246 switch from logic 1 to logic 0, and $Q_1=0$ remains held by the bistable 243. When A switches from $A=1$ to $A=0$, the outputs of the gates 250 and 246 switch from logic 0 to logic 1 so that a positive going edge is supplied to the bistable 243 which therefore sets and establishes $Q_1=1$. With $Q_1=1$ and $A=0$, gate 248 is rendered controllable by A, gate 249 closes gate 227 through gate 230, and gate 220 establishes logic 1 at the output of gate 221 so that gate 219 opens and clock pulses pass to the Y clock terminal 172, the diode 218 being non-conducting as in mode 2.

A second closure of switch S re-establishes $A=1$ whereupon the gate 248 causes the output of the gate 232 to switch from logic 0 to logic 1 and thus to set the bistable 231 so that $Q=1$ and $\overline{Q}=0$. Although the gate 249 is still open when A switches, its effect on gate 230 is slightly delayed by a resistance capacitance coupling as shown to the gate 230 so that $\overline{Q}=0$ closes gate 249 before $A=$ can affect gate 230.

It will also be seen from FIG. 13 that the CLOCK which is the source of clock pulses on the line 226 is only enabled when either gate 227 or gate 219 is open.

FIG. 14 shows the circuit of the input logic unit 30 and the switches 29 and S and P. It will be seen that the scan rate control knob 60 varies the time constant of the CLOCK which incorporates a Signetics 555 timer IC. The two bistables 231 and 243, each half of a 4013 IC, have D terminals, that of bistable 231 being fixed at logic 1 by connection to rail 152, and that of the bistable 243 being determined by the output of an inverter 251 whose input terminal is coupled through a diode 252 and a resistor to the switch P and is connected at a terminal 253 to the X start terminal 127 of FIG. 5. This ensures that the bistable 243 cannot be set while the slave start area ST is illuminated. The input terminal of the inverter 251 is also coupled to the ground rail 155 through a large resistor so that logic 1 is normally established at the D terminal of the bistable 243. Switch P is also disabled when any area of the $Y_0$ is illuminated, by being coupled at a terminal 254 to a terminal 255 coupled to the latch 70 of FIG. 5, a switch (not shown) which is closed for mode 40 only, by the mode switch 29, interconnecting the terminals 254 and 255. A further terminal 256 is likewise coupled to the terminal 255 in mode 3. These couplings ensure that areas in the $Y_0$ row cannot be selected as answers by the pupil.

It will also be seen that the terminal 130 in FIG. 5 is coupled by a diode to a terminal 257 of the review switch 26 of FIG. 8. This ensures that no area of row $Y_0$ can be illuminated when the review switch 26 is closed.

Referring now to FIG. 15, it will be seen that the comparator input terminal 89 to 94 of FIG. 5 are connected to four decoders (each being half of a 4555 IC) 258, 259, 260 and 261 which operate respectively as master row decoders for $R_1$, $R_2$, $R_3$ and $R_4$. The respective four row terminals in the patchboard master set 43 are coupled by diodes to the four output terminal of the respective master row decoder. Thus the master set 43 is made representative of the sixteen areas of the master array 21. The comparator slave input terminals 121 to 125 are connected as shown to two eight input multiplexers 262 and 263 with terminal 124 connected to the low enable terminal of the multipliexer 262, and the terminal 125 connected to the low enable terminal of the multiplexer 263. As a result, the eight other terminals of the multiplexer 262 are connected respectively to the first two rows of the slave set 44 to represent the slave array rows $Y_1$ and $Y_2$, and the eight other terminals of the multiplexer 263 are connected respectively to the second two rows of the slave set 44 $Y_3$ and $Y_4$. When the sets 43 and are interconnected, the multiplexers 262 and 263 produce a logic 0 at comparator output terminal 264 unless the signals at the master set 43 are matched by the signals which the multiplexers 262 and 263 require to be present at the slave set 44 to produce a logic 1 at the output terminal 264. The provision of isolating diodes at the master set 44 and grounded resistors at the slave set 44 as shown enables the comparator 41 to operate with a single connection between the master and slave sets 43 and 44.

FIG. 16 shows the output logic unit 36 in detail. The logic conditions of the ready state of the unit 36 are indicated in FIG. 16. In this ready state the unit 36 applies a high disabling signal at a tune control terminal 267 and a low disabling signal at another tune control terminal 268 to the tune generator 47. A low signal is applied at a buzz trigger terminal 269 to the buzz trigger terminal 269 to the buzz generator 49, and a high "buzz silent" signal (logic 1) is received from the buzz generator 49 at a buzz state terminal 270. A terminal 265 coupled to ground is connected to the OR gate 149 of the review unit 27, and a terminal 266 at logic 0 is connected to the reset terminals 238 and 244 of the bistables 231 and 243 of the input logic unit of FIG. 14. The slave register reset terminal 111 is provided with logic 0. A terminal 271 supplies logic 0 to the shift in terminal of the memory unit 51 and to the clock terminal of the mistakes counter and display unit 50. A terminal 272 supplies logic 1 to a low reset terminal of the memory unit 51. Before the ready state is established, on switching on the apparatus as capacitor-resistor combination 273 establishes logic 1 at 265, logic 0 at 272, and also logic 1 at 111 and 266.

In the ready state, the lamp 52 is "off" since its current is controlled by a NOR gate 274 which has logic 0 as output in this state.

When logic 1 appears at the "selection complete" terminal 234, ie Q=1 in FIG. 14, logic 1 is applied to an inverter 275, and consequently logic 0 is applied by the inverter 275 to open two NOR gates 276 and 277. If the comparator output terminal 264 then has logic 1, indicating a correct choice, this logic 1 is applied to the gate 277 and is inverted by an inverter to establish logic 0 at the gate 276. Consequently the state of a buzz trigger latch 278 controlled by the gate 277 is not changed, but a tune control monostable 279 is set by the output of gate 276. Setting this monostable isolates the tune control terminal 267, previously held at logic 1, and establishes logic 1 at the tune control terminal 268. A timing capacitor 280 then holds these signals at the terminals 267 and 268 while it gradually charges up until it re-establishes logic 1 at the terminal 267 and hence logic 0 at the terminal 268 through operation of the two NOR gates of the monostable 279.

When the last tune occurs, the signal at the terminal 102 goes to logic 0, a last tune latch 281 is set, the output of the gate 274 becomes logic 1 at the end of the last tune, and the lamp 52 is illuminated. Also the set latch 281 closes a NOR gate 282 which determines the signal on the input unit reset terminal 266.

A capacitor 283 coupled as shown to the tune latch 279, ground and two series inverters acting as a Schmitt circuit 284 causes logic 1 to appear at the master advance terminal 160 for a short time starting at resetting of the latch 279. Also, as a result, logic 1 is established by a NOR gate 285 acting through an inverter 286 at the slave resetting terminal 111.

If when the "selection complete" appears at the terminal 234, a wrong choice has been made by the pupil, logic 0 is present at the terminal 264. Consequently the output of the gate 276 remains unchanged. However, the output of the gate 277 changes from logic 0 to logic 1 so that the memory unit 51 stores the array addresses and the mistakes counter and display unit 50 record and display the occurrence of the mistake. Furthermore, the buzz trigger latch 278 is set and logic 1 appears at the buzz trigger terminal 269 and enables the buzz generator 49 to operate. At the end of the buzz, logic 0 appears for a short time at the terminal 270 so that an inverter 287 resets the buzz latch 278 and causes logic 1 to appear for the same short time at the slave resetting terminal 111 and the input unit reset terminal 266. The master advance terminal 160 remains at logic 0.

The master reset line 148 is also connected as shown to the monostable 279, the latch 281 and, through a NOR gate 288, to the gate 282. This allows appropriate resetting to occur when the review switch 26 is closed.

FIG. 17 shows the memory unit 51 which has a FIFO integrated circuit memory 289, type 3351, nine transistor output drives 290, four output decoders 291 to 294, and an output enable inverter 295 since the decoders 291 to 294 are the low enable type (each being half a 4555). The master reset line 148 is connected to the shift out input of the memory IC 289 and through the inverter 295 to the low enable terminals of the decoders 291 to 294. The terminal 271 is connected to the shift in terminal of the memory IC 289, and the terminal 272 is connected to its memory reset terminal.

The terminals 98 are connected to eight address input terminals of IC 289, the ninth address input terminal being connected to a terminal 296 of the latch 70 of FIG. 5 to record mistakes made by choosing an area in the slave row $Y_O$. The corresponding nine address output terminals are connected as shown to the respective transistor drivers 290. If when a review signal appears on the line 148, the output corresponding to a mistake recorded from the terminal 296 appears, at the lowest output terminal in FIG. 17, a high signal is applied to the enable terminals of all the decoders 291 to 294, directly to 291 and through a resistor 298 to 292, 293 and 294 so that this mistake does not result in any review display by the arrays 21 and 22. Other mistakes result, on review, in outputs at other ones of the address output terminals of the IC 289 which are appropriately decoded by a respective one of the four decoders 291 to 294.

FIG. 18 shows the circuit of the tune generator 47. When the tune monostable 279 of FIG. 16 is set and the terminal 268 is at logic 1, an astable circuit 299 operates, and enables a 50 kilohertz oscillator 300 to oscillate intermittently. A high speed counter 301, (type 4024), counts the output of the oscillator 300 and generates a staircase waveform at a summing junction 302 coupled to four of its outputs. The staircase waveform modulates the bias applied to a transistor 303 connected to discharge a capacitor 304 which, when terminal 267 is floating as is the case when monostable 279 is set, is charged in pulses by a transistor 305 controlled by negative logic feedback as shown from the capacitor 304. The voltage across the capacitor 304 is filtered and the filtered output coupled through an inverter 306 and a controlled attenuator network 307 to a tune output terminal 308. The control element in the attenuator 307 is a transistor 309 which modulates the attenuatation in accordance with the voltage on a timing capacitor 310 of the astable 299. This voltage is also controlled to some extent by feedback from two outputs of the counter 301.

FIG. 19 shows the buzz generator 49 and the amplifier 48 in detail.

The buzz generator 49 has a unijunction transistor 311, a capacitor 312 and transistor 313 coupled to establish oscillatory charging and discharging of the capacitor 312 during one cycle of an astable circuit 314 which is unclamped whenever logic 1 appears at the terminal 269. A timing capacitor 315 of the astable 314 provides the control voltage for the charging transistor 313 and the shape of this control voltage provides the "raspberry" effect of the sound. The voltage on the oscillator capacitor 312 is coupled by an output transistor 316 to the input transistor 317 of the amplifier 48. The tune output terminal 308 is also connected to input transistor 317 as shown. Thus the amplifier 48 amplifies either the buzz generator output or the time generator output depending on whichever is present. The volume control knob 53 controls an attenuator in the amplifier 48 as shown.

At the end of each cycle, the astable 314 generates a logic 0 pulse at the terminal 270 to terminate operation of the buzz generator 49 by resetting the latch 278.

FIG. 20 shows the circuit of the mistakes counter and display unit 50. Mistakes pulses on terminal 271 are supplied as clock pulses to a units counter 318 having its highest output supplied to the clock terminal of a tens counter 319. Four outputs of each counter 318 or 319 are supplied to a respective seven-segment decoder 320 or 321 driving a respective seven-segment display 322 or 323. Details of such circuitry will be well known to those skilled in the art and need not be further described.

I claim:

1. Apparatus for use in testing visual recognition, the apparatus comprising:

a first array of illuminating means individually selectable for energisation;

first register means coupled to the first array of illuminating means and adapted to select for energisation each illuminating means of the first array in accordance with a respective first predetermined sequence;

a second array of illuminating means individually selectable for energisation;

second register means coupled to the second array of illuminating means and adapted to select for energisation a chosen illuminating means in the second array;

mechanically controllable means for causing the said second register means to select for energisation in accordance with a respective second predetermined sequence a set of the illuminating means terminating with a chosen illuminating means and for establishing a signal indicative of selection of the said chosen illuminating means;

a first array of terminals representative of the said first array of illuminating means;

a second array of terminals representative of at least some of said second array of illuminating means, means for interconnecting at least one pair of said terminals, each such pair of terminals comprising one terminal from each of said arrays of terminals;

comparator means coupled to said register means and said interconnecting means to compare the contents of said register means in dependence upon the interconnection of terminals by said interconnecting means;

logic means coupled to said comparator means and to said mechanically controllable means whereby said comparator means is adapted to provide a first output signal in response to the said signal indicative of selection when there is correspondence between the contents of the second register means representing said chosen illuminating means and the contents of the first register means, and to provide a second output signal in response to the said signal indicative of selection when there is absence of such correspondence;

error memory means coupled to said register means and said arrays of illuminating means and to said logic means and adapted to store respective addresses for the selected illuminating means of the first array of illuminating means and the chosen illuminating means of the second array of illuminating means in response to the said second output signal; and review means coupled to the error memory means and actuable to cause said error memory means to establish energisation of respective illuminating means in said arrays of illuminating means in accordance with the respective stored addresses.

2. Apparatus as claimed in claim 1, wherein said logic means includes means for supplying an advance signal and coupled to said first register means to effect an advance in said first predetermined sequence at the occurrence of each advance signal and to said second register means to effect resetting of said second registry means to start condition at each occurrence of each advance signal.

3. Apparatus as claimed in claim 1, wherein said logic means includes means for supplying a reset signal to said second register means to effect resetting of said second register means to a start condition in response to each occurrence of said second output signal.

4. Apparatus as claimed in claim 1, further including audio signal generating means coupled to said logic means to generate a first audio signal in response to said first output signal and a second audio signal in response to said second output signal.

5. Apparatus as claimed in claim 2, further including audio signal generating means coupled to said logic means to generate a first audio signal in response to said first output signal, the said logic means including timing means adapted to terminate said first audio signal after a predetermined duration and to establish said advance signal on terminating said first audio signal.

6. Apparatus as claimed in claim 3, further including audio signal generating means coupled to said logic means to generate a second audio signal in response to said second output signal, said audio signal means including means for establishing said reset signal at termination of said second audio signal.

7. Apparatus as claimed in claim 1, wherein said mechanically controllable means includes clock pulse generating means, gating means coupling said clock pulse generating means to said second register means, and mechanically operable switch means connected to control said gating means so as to determine said second predetermined sequence.

8. Apparatus as claimed in claim 7, wherein said mechanically operable switch means includes mode switching means settable in any chosen one of a plurality of states, each such state determining a respective different form of said second predetermined sequence.

9. Apparatus as claimed in claim 8, wherein said mechanically operable switch means includes at least one switch which, for at least one state of said mode switching means, is adapted to be operable to establish said signal indicative of selection.

10. Apparatus as claimed in claim 9, wherein said switch is adapted to be operable, in at least one state of said mode switching means, to control the progress of at least part of said second predetermined sequence.

11. Apparatus as claimed in claim 10, including a further switch adapted to be operable in at least one state of said mode switching means to control the progress of at least part of said second predetermined sequence.

12. Apparatus as claimed in claim 11, wherein in one state of said mode switching means said one switch is operable to control the progress of an initial part of said second predetermined sequence and said further switch is operable to control the progress of a further part of said second predetermined sequence, said one switch being, after operation of said further switch, operable to establish said signal indicative of selection.

13. Apparatus as claimed in claim 9, wherein a further switch is adapted to be operable, in said one state of said mode switching means, to control the progress of said second predetermined sequence from starting to selection of said chosen illuminating means.

14. Apparatus as claimed in claim 8, wherein said mode switching means is settable in any chosen one of four states, each such state determining a respective different one of four forms of said second predetermined sequence, and said mechanically operable switch means includes two switches one of which is adapted to be operable to establish said signal indicative of selection in three of said four states and the other of which is adapted to be operable to establish said signal indicative of selection in the fourth of said four states.

15. Apparatus as claimed in claim 14, wherein said one switch is adapted to be operable to control the progress of the said second predetermined sequence in the said fourth state and to control at least part of the said progress in two of the said three states, and the said other switch is adapted to be operable to control the progress of part of the said progress in one of the said three states.

16. Apparatus as claimed in claim 8, wherein further gating means are so coupled to said mechanically operable switch means as to determine a respective condition for establishing of the said signal indicative of selection for each of said plurality of states.

17. Apparatus as claimed in claim 14, wherein said mode switching means comprises a manually operable rotary switch having four settings, and said two switches comprise two manually operable on-off switches.

18. Apparatus as claimed in claim 1, wherein each of said illuminating means comprises at least one electrically energisable light source.

19. Apparatus as claimed in claim 18, wherein means are provided for selectively determining the number of electrically energisable light sources comprising each illuminating means.

20. Apparatus for use in testing visual recognition, the apparatus comprising;
a first array of illuminating means individually selectable for energisation;
first register means coupled to the first array of illuminating means and adapted to select for energisation each illuminating means of the first array in accordance with a respective predetermined sequence;
a second array of illuminating means individually selectable for energisation;
second register means coupled to the second array of illuminating means and adapted to select for energisation a chosen illuminating means in the second array;
mechanically controllable means for causing the said second register means to select the energisation in accordance with a respective predetermined sequence a set of the illuminating means terminating with a chosen illuminating means and for establishing a signal indicative of selection of the said chosen illuminating means;
a first array of terminals representative of the said first array of illuminating means;
a second array of terminals representative of at least some of said second array of illuminating means, means for interconnecting at least one pair of said terminals, each such pair of terminals comprising one terminal from each of said arrays of terminals;
comparator means coupled to said register means and said interconnecting means to compare the contents of said register means in dependence upon the interconnection of terminals by said interconnecting means;
logic means coupled to said comparator means and to said manually controllable means whereby said comparator means is adapted to provide a first output signal in response to the said signal indicative of selection when there is correspondence between the contents of the second register means representing said chosen illuminating means and the contents of the first register means, and to provide a second output signal in response to the said signal indicative of selection when there is absence of such correspondence;
and audio signal generating means coupled to said logic means to generate a first audio signal in response to said first output signal and a second audio signal in response to said second output signal.

21. Apparatus as claimed in claim 20, wherein said audio signal generating means comprises tune generating circuitry adapted to operate in response to said first output signal, and buzz generating circuitry adapted to operate in response to said second output signal, whereby the first audio signal is a tune signal and the second audio signal is a buzz signal.

22. Apparatus as claimed in claim 21, wherein said logic means includes timing means arranged to determine the duration of operation of the tune generating circuitry in response to each first output signal, and the buzz generating circuitry includes further timing means arranged to determine the duration of operation of the buzz generating circuitry in response to each second output signal and to modulate the buzz signal.

23. Apparatus as claimed in claim 22, wherein said tune generating circuitry and said buzz generating circuitry are coupled to electro-acoustic transducing means whereby said tune and buzz signals are transduced into audible tunes and buzzes.

* * * * *

UNITED STATES PATENT AND TRADEMARK OFFICE
CERTIFICATE OF CORRECTION

PATENT NO. : 4,353,626
DATED : October 12, 1982
INVENTOR(S) : Leslie Herbert Raymond Harrison It is certified that error appears in the above-identified patent and that said Letters Patent are hereby corrected as shown below:

At column 22, line 6, change "the" to --for--

Signed and Sealed this

Seventh Day of June 1983

[SEAL]

Attest:

DONALD J. QUIGG

Attesting Officer

Acting Commissioner of Patents and Trademarks